United States Patent
Evans et al.

(10) Patent No.: US 9,957,272 B2
(45) Date of Patent: May 1, 2018

(54) 3-HYDROXYPYRROLIDINE INHIBITORS OF 5'-METHYLTHIOADENOSINE PHOSPHORYLASE AND NUCLEOSIDASE

(71) Applicants: VICTORIA LINK LIMITED, Wellington (NZ); ALBERT EINSTEIN COLLEGE OF MEDICINE, INC., Bronx, NY (US)

(72) Inventors: Gary Brian Evans, Normandale (NZ); Alistair Ian Longshaw, Nottingham (GB); Vern L. Schramm, New Rochelle, NY (US); Peter Charles Tyler, Northland (NZ)

(73) Assignees: Victoria Link Limited, Wellington (NZ); Albert Einstein College of Medicine, Inc., Bronx, NY (US)

( * ) Notice: Subject to any disclaimer, the term of this patent is extended or adjusted under 35 U.S.C. 154(b) by 0 days. days.

(21) Appl. No.: 15/347,944

(22) Filed: Nov. 10, 2016

(65) Prior Publication Data

US 2017/0166573 A1  Jun. 15, 2017

Related U.S. Application Data

(63) Continuation of application No. 13/383,772, filed as application No. PCT/NZ2010/000148 on Jul. 16, 2010, now Pat. No. 9,493,465.

(60) Provisional application No. 61/271,112, filed on Jul. 17, 2009.

(51) Int. Cl.
| | |
|---|---|
| C07D 487/04 | (2006.01) |
| A61K 31/519 | (2006.01) |
| A61P 35/00 | (2006.01) |
| A61P 31/04 | (2006.01) |
| A61P 33/02 | (2006.01) |

(52) U.S. Cl.
CPC ................. C07D 487/04 (2013.01)

(58) Field of Classification Search
CPC ............ C07D 487/04; A61K 31/519
See application file for complete search history.

(56) References Cited

U.S. PATENT DOCUMENTS

| | | |
|---|---|---|
| 5,985,848 A | 11/1999 | Furneaux et al. |
| 6,066,722 A | 5/2000 | Furneaux et al. |
| 6,228,847 B1 | 5/2001 | Furneaux et al. |
| 6,492,347 B2 | 12/2002 | Furneaux et al. |
| 6,693,193 B1 | 2/2004 | Furneaux et al. |
| 6,803,455 B2 | 10/2004 | Furneaux et al. |
| 7,022,852 B2 | 4/2006 | Furneaux et al. |
| 7,098,334 B2 | 8/2006 | Furneaux et al. |
| 7,109,331 B2 | 9/2006 | Furneaux et al. |
| 7,211,653 B2 | 5/2007 | Furneaux et al. |
| 7,211,677 B2 | 5/2007 | Furneaux et al. |
| 7,390,890 B2 | 6/2008 | Furneaux et al. |
| 7,405,297 B2 | 7/2008 | Furneaux et al. |
| 7,553,839 B2 | 6/2009 | Evans et al. |
| 7,655,795 B2 | 2/2010 | Evans et al. |
| 2008/0280334 A1 | 11/2008 | Lenz et al. |
| 2009/0012104 A1 | 1/2009 | Babu et al. |
| 2009/0233948 A1 | 9/2009 | Evans et al. |
| 2009/0239885 A1 | 9/2009 | Evans et al. |
| 2009/0325986 A1 | 12/2009 | Furneaux et al. |
| 2010/0062995 A1 | 3/2010 | Schramm |
| 2010/0094003 A1 | 4/2010 | Evans et al. |
| 2010/0168141 A1 | 7/2010 | Evans et al. |
| 2010/0222370 A1 | 9/2010 | Schramm et al. |
| 2011/0046167 A1 | 2/2011 | Clinch et al. |
| 2011/0086812 A1 | 4/2011 | Schramm |
| 2011/0092521 A1 | 4/2011 | Furneaux et al. |
| 2011/0130412 A1 | 6/2011 | Clinch et al. |
| 2011/0190265 A1 | 8/2011 | Schramm |

FOREIGN PATENT DOCUMENTS

| | | |
|---|---|---|
| WO | 2004018496 A1 | 3/2004 |
| WO | 2006014913 A2 | 2/2006 |
| WO | 2007069923 A1 | 6/2007 |
| WO | 2007097647 A1 | 8/2007 |
| WO | 2009082247 | 7/2009 |

OTHER PUBLICATIONS

Longshaw A L et al., entitled "Design and Synthesis of Potent "Sulfur-free" Transition State Analogue Inhibitors of 5'-Methylthioadenosine Nucleosidase and 5'-Methylthioadensine Phosphorylase," J Med Chem, Sep. 23, 2010; 53(18): 6730-6746.
Patent Examination Report No. 1, dated Jan. 7, 2015 from the IP Australia in connection with Australian Patent Application No. 2010271532, 4 pages.
Final Rejection dated Apr. 7, 2015 in connection with Japanese Patent Application No. P2012-520557, 3 pages.
Communication Pursuant to Article 94(3) EPC, dated Mar. 9, 2015 from the European Patent Office in connection with European Patent Application No. 10 800 093.6, 5 pages.
Communication issued by the European Patent Office dated Nov. 22, 2013 in connection with European Patent Application No. 10800096.6, 5 pages.
Evans GB, et al., "Second Generation Transition State Analogue Inhibitors of Human 5'-Methylthioadenosine Phosphorylase", J. Med. Chem. 2005, 48, 4679-4689.
Singh V, et al., "Femtomolar Transition State Analogue Inhibitors of 5'-Methylthioadenosine/S-Adenosylhomocysteine Nucleosidase from *Escherichia coli*", The Journal of Biological Chemistry, vol. 280, No. 18, Issue of May 6, 2005, pp. 18265-18273, Epub Mar. 4, 2005.
Singh V, et al., "Structure and Inhibition of a Quorum Sensing Target from *Streptococcus pneumoniae*", Biochemistry, Oct. 31, 2006; 45(43): 12929-12941.

(Continued)

*Primary Examiner* — Susanna Moore
(74) *Attorney, Agent, or Firm* — Amster, Rothstein & Ebenstein LLP

(57) ABSTRACT

The present invention relates to 3-hydroxypyrrolidine compounds of the general formula (1) which are inhibitors of 5'-methylthioadenosine phosphorylase or 5'-methylthioadenosine nucleosidase. The invention also relates to the use of these compounds in the treatment of diseases or conditions in which it is desirable to inhibit 5'-methylthioadenosine phosphorylase or 5'-methylthioadenosine nucleosidase including cancer, and to pharmaceutical compositions containing the compounds.

8 Claims, No Drawings

(56) References Cited

OTHER PUBLICATIONS

Notice of Reasons for Rejections dated Jul. 22, 2014 in connection with Japanese Patent Application No. P2012-520557, 11 pages.
Evans et al., Organic Letters, 2003, 5(20), pp. 3639-3640.
Communicaiton Supplementary European Search Report dated Nov. 14, 2012 in connection with European Patent Application No. 10800096.6, 8 pages.
Liu H et al., entitled "QSAR study on 5'methylthioadenosine nucleosidase inhibitors," Journal of Dalian Polytechnic University (2008),27(1), 10-14.
Canadian Office Action dated Feb. 14, 2017 in connection with Canadian Application No. 2,768,291, 4 pages.

3-HYDROXYPYRROLIDINE INHIBITORS OF 5'-METHYLTHIOADENOSINE PHOSPHORYLASE AND NUCLEOSIDASE

CROSS-REFERENCE TO RELATED APPLICATIONS

This application is a continuation of U.S. patent application Ser. No. 13/383,772, filed Mar. 1, 2012, now U.S. Pat. No. 9,493,465 B2, which is a national stage entry under 35 U.S.C. § 371 of PCT International Patent Application No. PCT/NZ2010/000148, filed Jul. 16, 2010, which claims priority to U.S. Provisional Patent Application No. 61/271,112, filed Jul. 17, 2009, the contents of which are incorporated herein by reference in their entirety.

STATEMENT OF GOVERNMENT SUPPORT

This invention was made with government support under grant numbers GM041916 and CA135405 awarded by the National Institutes of Health. The government has certain rights in the invention.

TECHNICAL FIELD

This invention relates generally to certain nucleoside analogues, the use of these compounds as pharmaceuticals, pharmaceutical compositions containing the compounds, processes for preparing the compounds, and methods of treating diseases or conditions in which it is desirable to inhibit 5'-methylthioadenosine phosphorylase or 5'-methylthioadenosine nucleosidase.

BACKGROUND

U.S. Pat. Nos. 5,985,848, 6,066,722 and 6,228,741 describe nucleoside analogues that are inhibitors of purine nucleoside phosphorylases (PNPs) and purine phosphoribosyl-transferases (PRTs). The analogues are useful in treating parasitic infections, T-cell malignancies, autoimmune diseases and inflammatory disorders. The analogues are also useful for immunosupression in organ transplantation.

U.S. Pat. No. 6,693,193 describes a process for preparing certain PNP inhibitor compounds. This application recognises the compounds as PNP inhibitors and addresses a need for simpler methods of preparing them. U.S. Ser. No. 10/363,424 discloses further nucleoside analogues that are inhibitors of PNPs and PRTs.

PNPs catalyse the phosphorolytic cleavage of ribo- and deoxyribonucleosides, for example those of guanine and hypoxanthine, to give the corresponding sugar-1-phosphate and guanine, hypoxanthine or other purine bases.

Humans deficient in PNP suffer a specific T-cell immunodeficiency due to an accumulation of dGTP which prevents proliferation of stimulated T lymphocytes. Inhibitors of PNP are therefore immunosuppressive, and are active against T-cell malignancies and T-cell proliferative disorders.

Nucleoside hydrolases (NHs) catalyse the hydrolysis of nucleosides. These enzymes are not found in mammals but are required for nucleoside salvage in some protozoan parasites. Some protozoan parasites use nucleoside phosphorylases either instead of or in addition to nucleoside hydrolases for this purpose. Inhibitors of nucleoside hydrolases and phosphorylases can be expected to interfere with the metabolism of the parasite and can therefore be usefully employed against protozoan parasites.

5'-Methylthioadenosine phosphorylase (MTAP) and 5'-methylthioadenosine nucleosidase (MTAN) function in the polyamine biosynthesis pathway, in purine salvage in mammals, and in the quorum sensing pathways in bacteria. MTAP catalyses the reversible phosphorolysis of methylthioadenosine (MTA) to adenine and 5-methylthio-α-D-ribose-1-phosphate (MTR-1P). MTAN catalyses the reversible hydrolysis of MTA to adenine and 5-methylthio-α-D-ribose, and of S-adenosyl-L-homocysteine (SAH) to adenine and S-ribosyl-homocysteine (SRH). The adenine formed is subsequently recycled and converted into nucleotides. Essentially, the only source of free adenine in the human cell is a result of the action of these enzymes. The MTR-1P is subsequently converted into methionine by successive enzymatic actions.

MTA is a by-product of the reaction involving the transfer of an aminopropyl group from decarboxylated S-adenosylmethionine to putrescine during the formation of spermidine. The reaction is catalyzed by spermidine synthase. Likewise, spermine synthase catalyses the conversion of spermidine to spermine, with concomitant production of MTA as a by-product. The spermidine synthase is very sensitive to product inhibition by accumulation of MTA. Therefore, inhibition of MTAP or MTAN severely limits the polyamine biosynthesis and the salvage pathway for adenine in the cells.

Although MTAP is abundantly expressed in normal cells and tissues, MTAP deficiency due to a genetic deletion has been reported with many malignancies. The loss of MTAP enzyme function in these cells is known to be due to homozygous deletions on chromosome 9 of the closely linked MTAP and p16/MTS1 tumour suppressor gene. As absence of p16/MTS1 is probably responsible for the tumour, the lack of MTAP activity is a consequence of the genetic deletion and is not causative for the cancer. However, the absence of MTAP alters the purine metabolism in these cells so that they are mainly dependent on the de novo pathway for their supply of purines.

MTA has been shown to induce apoptosis in dividing cancer cells, but to have the opposite, anti-apoptotic effect on dividing normal cells such as hepatocytes (E. Ansorena et al., Hepatology, 2002, 35: 274-280). MTAP inhibitors may therefore be used in the treatment of cancer. Such treatments are described in U.S. Ser. No. 10/395,636 and U.S. Ser. No. 10/524,995. Compounds where the location of the nitrogen atom in the sugar ring is varied or where two nitrogen atoms form part of the sugar ring, have also been identified as inhibitors of MTAP and MTAN. These compounds are described in U.S. Ser. No. 10/524,995.

The need for new cancer therapies remains ongoing. For some prevalent cancers the treatment options are still limited. Prostate cancer, for example, is the most commonly diagnosed non-skin cancer in the United States. Current treatment options include radical prostatectomy, radiation therapy, hormonal therapy, and watchful waiting. Although the therapies may offer successful treatment of an individual's condition, the pitfalls are quite unfavorable and lead to a decrease in a man's overall quality of life. Surgery may inevitably result in impotence, sterility, and urinary incontinence. Side effects associated with radiation therapy include damage to the bladder and rectum as well as slow-onset impotence. Hormonal therapy will not cure the cancer and eventually most cancers develop a resistant to this type of therapy. The major risk associated with watchful waiting is that it may result in tumour growth, cancer progression and metastasis. It is therefore desirable that alternative treatment options are made available to patients diagnosed with prostate cancer.

MTAP and MTAN inhibitors may also be used in the treatment of diseases such as bacterial infections or protozoal parasitic infections, where it is desirable to inhibit MTAP/MTAN. Such treatments are described in U.S. Ser. Nos. 10/395,636 and 10/524,995. However, the search continues for more effective treatments using these inhibitors.

The imino sugar part of the compounds described in the patent specifications referred to above has the nitrogen atom located between C-1 and C-4 so as to form 1,4-dideoxy-1,4-imino-D-ribitol compounds. The location of the nitrogen atom in the ribitol ring may be critical for binding to MTAP and MTAN enzymes. In addition, the location of the link between the sugar moiety and the nucleoside base analogue may be critical for enzyme inhibitory activity. The compounds described above have that link at C-1 of the sugar ring.

The applicants have also developed other MTAP and MTAN inhibitors, where the location of the nitrogen atom in the sugar ring is varied and, additionally, where two nitrogen atoms form part of the sugar ring. Alternative modes of linking the sugar part and the base analogue have also been investigated, resulting in a class of inhibitors where the sugar moiety is linked to the nucleoside base analogue via a methylene bridge. These other inhibitors are described in U.S. Ser. No. 10/395,636.

It has been considered to date that the three dimensional structure of the imino sugar ring of the above compounds is critical for effective binding to MTAP and MTAN, and therefore inhibition of these enzymes. The ring structure constrains the spatial locations that important functional groups, such as the imino nitrogen and various hydroxyl groups, can adopt when interacting with the enzymes.

The applicants have found that certain nucleoside analogue compounds, where the $CH_2SR$ substituents that are present in previously disclosed compounds are replaced by other moieties, are effective inhibitors of MTAN and/or MTAP.

Several of the previously reported MTAN and/or MTAP inhibitors have been shown to have short half-lives in in vivo experiments (e.g. in mice, as judged by persistence of MTAP inhibition). It is considered that this is due to biological conversion of the inhibitor into a non-inhibitor substance by, e.g. oxidation at sulfur.

It is therefore an object of the present invention to provide 3-hydroxy-pyrrolidine compounds that are inhibitors of MTAP or MTAN, or to at least provide a useful choice.

SUMMARY OF INVENTION

In a first aspect, the present invention provides a compound of the formula (I):

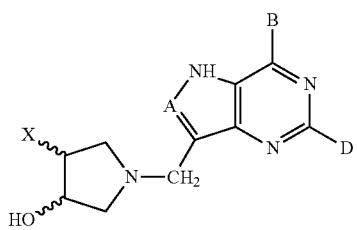

(I)

where:

X is an alkyl, cycloalkyl, alkenyl, alkynyl or aryl group, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino; hydroxy or alkoxy groups; or X is $SR^1$; or X is $NR^2R^3$;

$R^1$, $R^2$ and $R^3$ are independently selected from the group consisting of alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, cyano or $NR^2R^3$ group, where each alkylthio, arylthio and aralkylthio group is optionally substituted with one or more alkyl, halogen, amino, hydroxy, or alkoxy groups;

A is N or CH;

B is $NH_2$ or $NHR^5$;

$R^5$ is an alkyl, alkenyl, alkynyl, aralkyl, aralkenyl, aralkynyl or aryl group, each of which is optionally substituted with one or more halogen or hydroxy groups; and D is H, OH, $NH_2$, or $SCH_3$;

or a tautomer thereof, or a pharmaceutically acceptable salt thereof, or an ester prodrug form thereof;

provided that when B is $NH_2$, D is H and A is CH, X is not propyl, phenylethyl, $CH_2SQ$, $CH_2OH$ or $CH_2OQ$, where Q is an optionally substituted alkyl, aralkyl or aryl group.

In a second aspect, the present invention provides a compound of the formula (Ia):

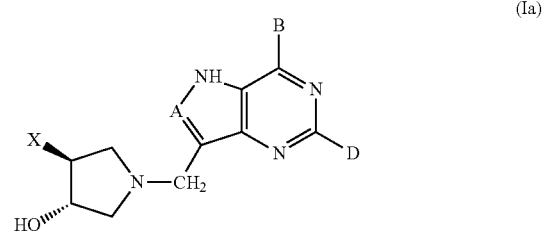

(Ia)

where:

X is an alkyl, cycloalkyl, alkenyl, alkynyl or aryl, group each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy or alkoxy groups; or X is $SR^1$; or X is $NR^2R^3$;

$R^1$, $R^2$ and $R^3$ are independently selected from the group consisting of alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, cyano or $NR^2R^3$ group, where each alkylthio, arylthio and aralkylthio group is optionally substituted with one or more alkyl, halogen, amino, hydroxy or alkoxy groups;

A is N or CH;

B is $NH_2$ or $NHR^5$;

$R^5$ is an alkyl, alkenyl, alkynyl, aralkyl, aralkenyl, aralkynyl or aryl group, each of which is optionally substituted with one or more halogen or hydroxy groups; and D is H, OH, $NH_2$, or $SCH_3$;

or a tautomer thereof, or a pharmaceutically acceptable salt thereof, or an ester prodrug form thereof;

provided that when B is $NH_2$, D is H and A is CH, X is not propyl, phenylethyl, $CH_2SQ$, $CH_2OH$ or $CH_2OQ$, where Q is an optionally substituted alkyl, aralkyl or aryl group.

In a third aspect the invention provides a compound of formula (Ib):

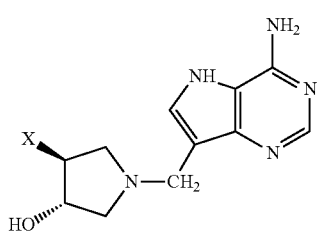

where X is as defined above;

provided that X is not propyl, phenylethyl, $CH_2SQ$, $CH_2OH$ or $CH_2OQ$, where Q is an optionally substituted alkyl, aralkyl or aryl group.

In another aspect the invention provides a compound of the formula (Ic):

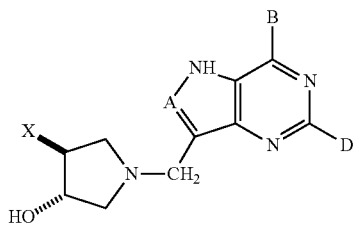

where:

X is an alkyl, cycloalkyl, alkenyl, alkynyl or aryl group, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy or alkoxy groups; or X is SW; or X is $NR^2R^3$;

$R^1$, $R^2$ and $R^3$ are independently selected from the group consisting of alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, cyano or $NR^2R^3$ group, where each alkylthio, arylthio and aralkylthio group is optionally substituted with one or more alkyl, halogen, amino, hydroxy or alkoxy groups;

A is N or CH;

B is $NH_2$ or $NHR^5$;

$R^5$ is an alkyl, alkenyl, alkynyl, aralkyl, aralkenyl, aralkynyl, or aryl group, each of which is optionally substituted with one or more halogen or hydroxy groups; and D is H, OH, $NH_2$, or $SCH_3$;

or a tautomer thereof, or a pharmaceutically acceptable salt thereof, or an ester prodrug form thereof;

provided that when B is $NH_2$, D is H and A is CH, X is not propyl, phenylethyl, $CH_2SQ$, $CH_2OH$ or $CH_2OQ$, where Q is an optionally substituted alkyl, aralkyl or aryl group.

In some examples of the above formulae (I), (Ia), (Ib) and (Ic), Q is an optionally substituted alkyl, aralkyl or aryl group. For example, Q may be optionally substituted with one or more: halogens, e.g. chlorine or fluorine;

alkyl groups, e.g. methyl or cyclohexylmethyl;

COOH; or $NH_2$.

In some examples of the above formulae (I), (Ia), (Ib) and (Ic), X is an alkenyl or alkynyl group each of which is optionally substituted with one or more substituents selected from the group consisting of hydroxy, alkoxy, thiol, alkylthio, arylthio, aralkylthio, halogen, carboxylic acid, carboxylate alkyl ester, nitro, or $NR^2R^3$ group, where each alkylthio, arylthio and aralkylthio group is optionally substituted with one or more alkyl, halogen, amino, hydroxy, or alkoxy groups. X may be, for example, a lower alkenyl group, e.g. a vinyl, allyl or prop-1-en-2-yl group. X may be, for example, a lower alkynyl group, e.g. an ethynyl group or a propyn-3-yl group.

In other examples of the above formulae (I), (Ia), (Ib) and (Ic), X is an alkyl group which is optionally substituted with one or more substituents selected from the group consisting of hydroxy, alkoxy, thiol, alkylthio, arylthio, aralkylthio, e.g benzylthio, halogen, carboxylic acid, carboxylate alkyl ester, nitro or $NR^2R^3$ group, where each alkylthio, arylthio and aralkylthio group is optionally substituted with one or more alkyl, halogen, amino, hydroxy or alkoxy groups. X may be, for example, a lower alkyl group, e.g., ethyl, butyl, isobutyl, pent-3-yl or an alkyl group substituted with a cycloalkyl group, e.g. cyclohexyl group, e.g. X may be cyclohexanemethyl. Alternatively, X may be, for example, alkyl group which is substituted with an aralkylthio group, e.g X may be benzylthiopropyl.

In other examples of the above formulae (I), (Ia), (Ib) and (Ic), X is an alkyl group which is optionally substituted with one or more substituents selected from the group consisting of cycloalkyl, e.g. cycloalkyl in which one or more of the ring carbon atoms is substituted by a heteroatom chosen from nitrogen, oxygen or sulfur. In some examples, X may be cyclopropanemethyl, 2-tetrahydrofuranmethyl, 2-thietanemethyl, 3-piperidinemethyl, 2-pyrrolidinemethyl or 4-thiacyclohexanemethyl.

In other examples of the above formulae (I), (Ia), (Ib) and (Ic), X is a cycloalkyl group which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy or alkoxy groups. X may be, for example, a cyclopropyl, cyclobutyl, cyclopentyl, cyclohexyl or adamantyl group.

X may be a cycloalkyl group where one or more of the ring atoms is a heteroatom, e.g. a nitrogen, sulfur or oxygen atom. X may be, for example, 2-tetrahydrofuranyl, 2-tetrahydrothienyl, 1,2-dithian-3-yl, piperidin-3-yl, thietan-2yl, 2-pyrrolidinyl or 4-thiacyclohexyl.

In other examples of the above formulae (I), (Ia), (Ib) and (Ic), X is an aryl group which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy, or alkoxy groups. The aryl group may be a heteroaryl group, where one or more of the ring carbon atoms is a heteroatom, e.g. a nitrogen, sulfur or oxygen atom. X may be, for example, a phenyl group or an optionally substituted triazole group. Where X is an optionally substituted triazole group the triazole ring may optionally be substituted with one or more substituents selected from the group consisting of aryl group, e.g. phenyl; alkyl group, e.g. a lower alkyl group, e.g. a propyl group which may optionally be substituted with one or more substituents selected from aryl, hydroxyl, or alkoxy; aralkyl group, e.g. benzyl; or cycloalkyl group. Where X is an optionally substituted triazole group the triazole ring may be attached to the pyrrolidine ring via either a triazole ring nitrogen or a triazole ring carbon atom.

In other examples of the above formulae (I), (Ia), (Ib) and (Ic), X is $SR^1$, where $R^1$ is alkyl, alkenyl, alkynyl, aralkyl or aryl, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy or alkoxy groups. For example, X may be phenylthio, 4-chlorophenylthio, 4-fluorophenylthio, 3-fluorophenylthio, 4-methylphenylthio, ethylthio, propylthio, pentylthio, 3-fluoropropylthio, 2,3-dihydroxypropylthio, 3-hydroxypropylthio, 2-hydroxyethylthio, allylthio or 4-chlorobutylthio.

In other examples of the above formulae (I), (Ia), (Ib) and (Ic), X is $NR^2R^3$, where $R^2$ and $R^3$ are independently selected from alkyl, alkenyl, alkynyl, aralkyl or aryl, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy, or alkoxy groups. For example, X may be diethylamino, ethylamino, propylamino, butylamino, 2-hydroxyethylamino, 3-hydroxypropylamino, 2,3-dihydroxypropylamino, 3-fluoroethylamino, trifluoroethylamino, bis(2-hydroxyethyl)amino, 3-butenylamino, benzylamino, 4-fluorobenzylamino, 4-chlorobenzylamino, or N-methyl-benzylamino.

In some examples of the above formulae (I), (Ic) and (Ia), B is $NH_2$. In some examples of the above formulae (I), (Ic) and (Ia), D is H. In some examples of the above formulae (I) and (Ia), B is $NH_2$ and D is H.

In some examples of the above formulae (I), (Ic) and (Ia), A is CH. In other examples of the above formulae (I), (Ic) and (Ia), A is N.

In some examples of the above formulae (I), (Ia), (Ib) and (Ic), X is an optionally substituted alkyl group, where the alkyl group may be substituted by one or more hydroxy groups. For example, X may be hydroxymethyl, hydroxyethyl, hydroxypropyl, dihydroxypropyl, hydroxybutyl, dihydroxybutyl, trihyroxybutyl, hydroxypentyl, dihydroxypentyl, or trihydroxypentyl.

In other examples of the above formulae (I), (Ia), (Ib) and (Ic), X is an alkyl group substituted by one or more thiol, alkylthio, arylthio, or aralkylthio groups. For example, X may be methylthiomethyl, methylthioethyl, methylthiopropyl, methylthiohydroxypropyl, methylthiodihydroxypropyl, methylthiobutyl, methyithiohydroxybutyl, methylthiodihydroxybutyl, methylthiotrihydroxybutyl, methylthiopentyl, methyithiohydroxypentyl, methyithiodihydroxypentyl, methylthiotrihydroxypentyl or methylthiotetrahydroxypentyl.

In some examples of the above formulae (I), (Ia), (Ib) and (Ic), X is an optionally substituted alkyl group, where the alkyl group may be substituted by a cycloalkyl group, e.g. a cycloalkyl group where one or more of the ring atoms is a heteroatom, e.g. a nitrogen, sulfur or oxygen atom. For example, X may be an alkyl group which is substituted with aziridinyl group, thiiranyl group, 1,2-dithietanyl group, azetidinyl group or epoxide group.

In some examples of the above formulae (I), (Ic) and (Ia) D is OH, $NH_2$ or $SCH_3$.

In some examples, substituents X and OH on the hydroxypyrrolidine ring are trans to each other. In other examples, substituents X and OH on the hydroxypyrrolidine ring are cis to each other. In some examples, compounds of formula (I) and (Ic) have stereochemistry with respect to substituents X and OH at positions 3 and 4 of the pyrrolidine ring that is the same as the stereochemistry of Compound 20 of Example 12.

In another aspect, the invention provides a compound selected from the group consisting of:
i. (±)-trans-1-[(9-Deaza-adenin-9-yl)methyl]-3-hydroxy-4-phenylpyrrolidine;
ii. (±)-trans-1-[(9-Deaza-adenin-9-yl)methyl]-3-hydroxy-4-vinylpyrrolidine;
iii. (±)-trans-1-[(9-Deaza-adenin-9-yl)methyl]-4-ethenyl-3-hydroxypyrrolidine;
iv. (±)-trans-4-Allyl-1-[(9-deaza-adenin-9-yl)methyl]-3-hydroxypyrrolidine;
v. (±)-trans-4-Cyclopropyl-1-[(9-deaza-adenin-9-yl)methyl]-3-hydroxypyrrolidine;
vi. (±)-trans-4-Cyclohexyl-1-[(9-deaza-adenin-9-yl)methyl]-3-hydroxypyrrolidine;
vii. (±)-trans-4-Cyclohexylmethyl-1-[(9-deaza-adenin-9-yl)methyl]-3-hydroxypyrrolidine;
viii. (±)-trans-1-[(9-Deaza-adenin-9-yl)methyl]-3-hydroxy-4-prop-1-en-2-yl-pyrrolidine;
ix. (±)-trans-1-[(9-Deaza-adenin-9-yl)methyl]-4-ethyl-3-hydroxypyrrolidine;
x. (±)-trans-4-Butyl-1-[(9-Deaza-adenin-9-yl)methyl]-3-hydroxypyrrolidine;
xi. (±)-trans-1-[(9-Deaza-adenin-9-yl)methyl]-3-hydroxy-4-pent-3-yl-pyrrolidine;
xii. (3R,4S)-1-[(9-Deaza-adenin-9-yl)methyl]-4-ethyl-3-hydroxypyrrolidine;
xiii. (±)-trans-4-Cyclopentyl-1-[(9-deaza-adenin-9-yl)methyl]-3-hydroxypyrrolidine;
xiv. (±)-trans-1-[(9-Deaza-adenin-9-yl)methyl]-3-hydroxy-4-(1H-1,2,3-triazol-1-yl)pyrrolidine;
xv. (±)-trans-4-(1-Benzyl-1H-1,2,3-triazol-4-yl)-1-[(9-deaza-adenin-9-yl)methyl]-3-hydroxypyrrolidine;
xvi. (±)-trans-4-(3-Benzylthiopropyl)-1-[(9-deaza-adenin-9-yl)methyl]-3-hydroxypyrrolidine;
xvii. (3R,4S)-4-Butyl-1-[(9-Deaza-adenin-9-yl)methyl]-3-hydroxypyrrolidine;

xviii. (±)-cis-1-[(9-Deaza-adenin-9-yl)methyl]-4-ethyl-3-hydroxypyrrolidine;
xix. (3R,4S)-1-[(9-Deaza-adenin-9-yl)methyl]-3-hydroxy-4-phenylpyrrolidine;
xx. (3R,4S)-1-[(9-Deaza-adenin-9-yl)methyl]-3-hydroxy-4-vinylpyrrolidine;
xxi. (3R,4S)-1-[(9-Deaza-adenin-9-yl)methyl]-4-ethenyl-3-hydroxy-pyrrolidine;
xxii. (3R,4S)-4-Allyl-1-[(9-deaza-adenin-9-yl)methyl]-3-hydroxypyrrolidine;
xxiii. (3R,4S)-4-Cyclopropyl-1-[(9-deaza-adenin-9-yl)methyl]-3-hydroxypyrrolidine;
xxiv. (3R,4S)-4-Cyclohexyl-1-[(9-deaza-adenin-9-yl)methyl]-3-hydroxypyrrolidine;
xxv. (3R,4S)-4-Cyclohexylmethyl-1-[(9-deaza-adenin-9-yl)methyl]-3-hydroxypyrrolidine;
xxvi. (3R,4S)-1[(9-Deaza-adenin-9-yl)methyl]-3-hydroxy-4-prop-1-en-2-yl-pyrrolidine;
xxvii. (3R,4S)-4-Butyl-1-[(9-deaza-adenin-9-yl)methyl]-3-hydroxypyrrolidine;
xxviii. (3R,4S)-1-[(9-Deaza-adenin-9-yl)methyl]-3-hydroxy-4-pent-3-yl-pyrrolidine;
xxix. (3R,4S)-4-Cyclopentyl-1-[(9-deaza-adenin-9-yl)methyl]-3-hydroxypyrrolidine;
xxx. (3S,4S)-1-[(9-Deaza-adenin-9-yl)methyl]-3-hydroxy-4-(1H-1,2,3-triazol-1-yl)pyrrolidine;
xxxi. (3R,4R)-4-(1-Benzyl-1H-1,2,3-triazol-4-yl)-1-[(9-deaza-adenin-9-yl)methyl]-3-hydroxypyrrolidine;
xxxii. (3R,4S)-4-(3-Benzylthiopropyl)-1-[(9-deaza-adenin-9-yl)methyl]-3-hydroxypyrrolidine;
xxxiii. (3S,4S)-1-[(9-Deaza-adenin-9-yl)methyl]-4-ethyl-3-hydroxypyrrolidine;
xxxiv. (±)-trans-1-[(9-Deaza-adenin-9-yl)methyl]-3-hydroxy-4-(2-methylpropyl)pyrrolidine;
xxxv. (3R,4S)-1-[(9-Deaza-adenin-9-yl)methyl]-3-hydroxy-4-(2-methylpropyl)pyrrolidine;
xxxvi. (±)-trans-4-Butyl-1-[(9-deaza-adenin-9-yl)methyl]-3-hydroxypyrrolidine;
xxxvii. (3R,4S)-4-Butyl-1-[(9-deaza-adenin-9-yl)methyl]-3-hydroxypyrrolidine:
xxxviii. (±)-trans-1-[(9-Deaza-adenin-9-yl)methyl]-3-hydroxy-4-(thiazol-2-yl)-pyrrolidine;
xxxix. (3R,4S)-1-[(9-Deaza-adenin-9-yl)methyl]-3-hydroxy-4-(thiazol-2yl)-pyrrolidine
xl. (±)-trans-1-[(9-Deaza-adenin-9-yl)methyl]-3-hydroxy-4-(tetrazol-5-yl)-pyrrolidine; and
xli. (3R,4R)-1-[(9-Deaza-adenin-9-yl)methyl]-3-hydroxy-4-(tetrazol-5-yl)-pyrrolidine;

or a tautomer thereof, or a pharmaceutically acceptable salt thereof, or an ester prodrug form thereof.

In another aspect the invention provides a compound selected from the group consisting of:

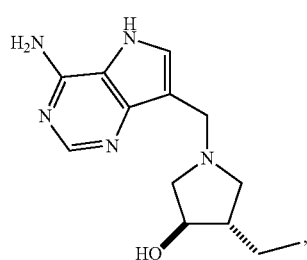

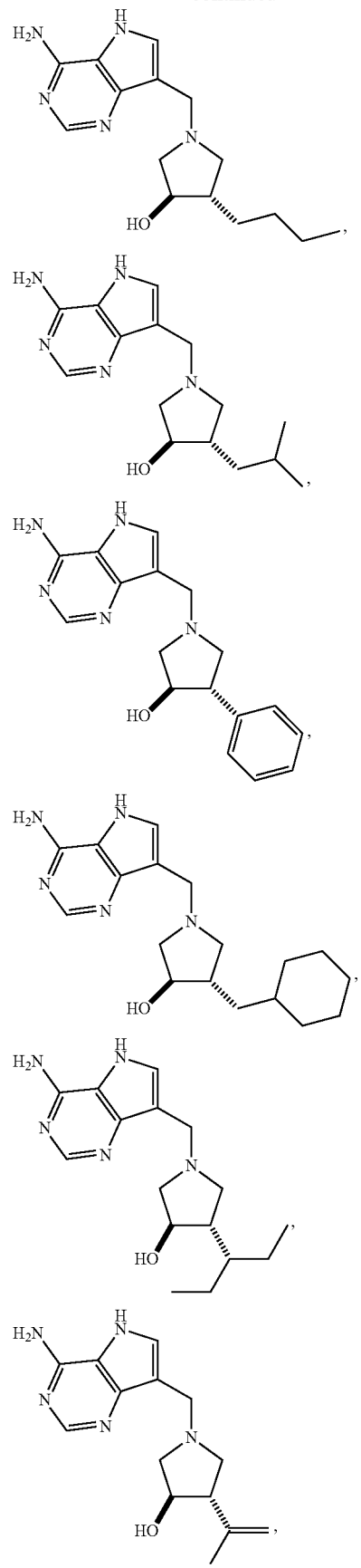

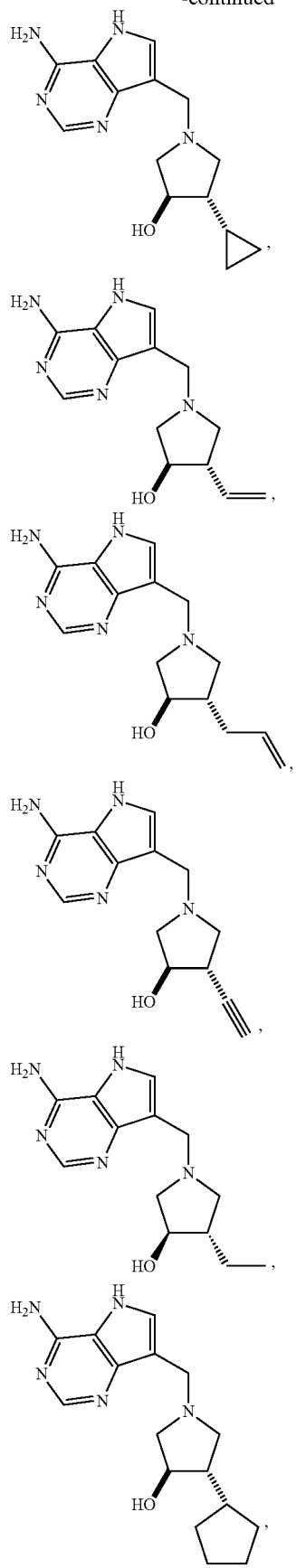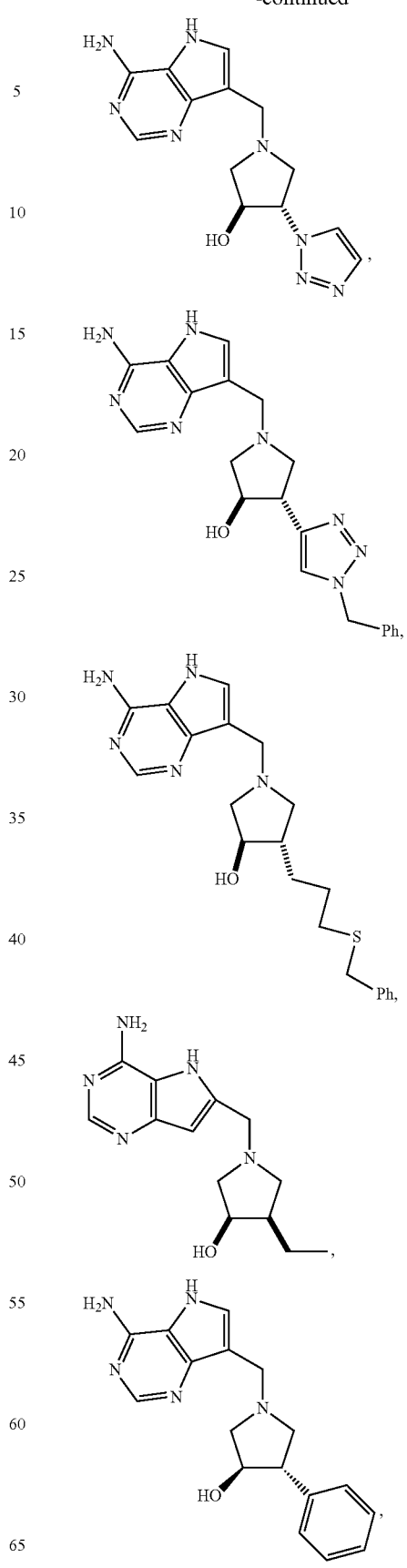

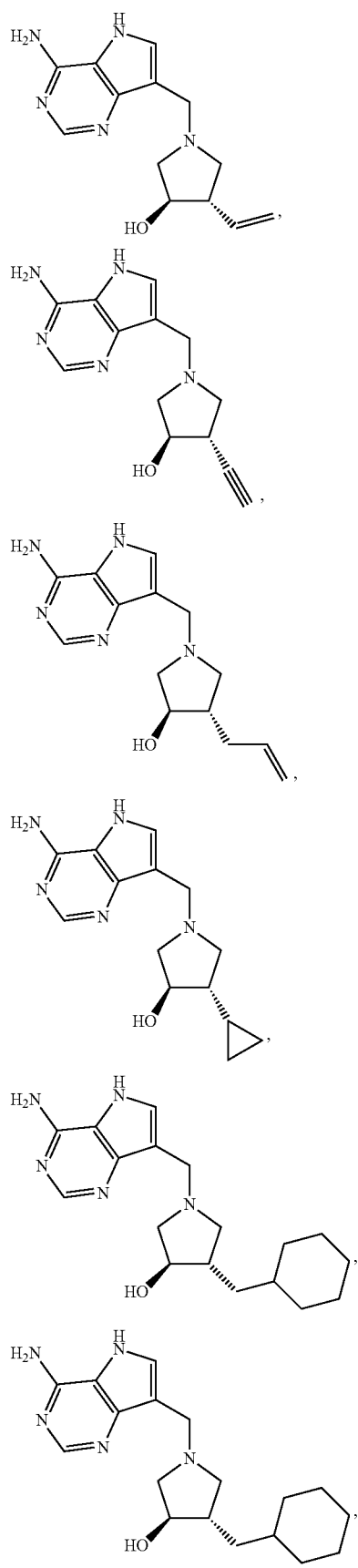
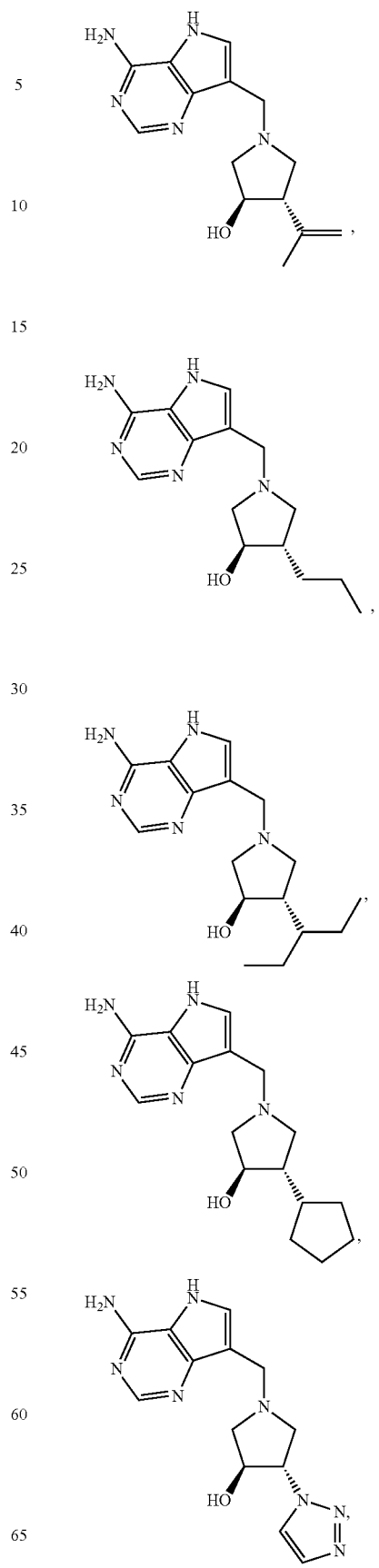

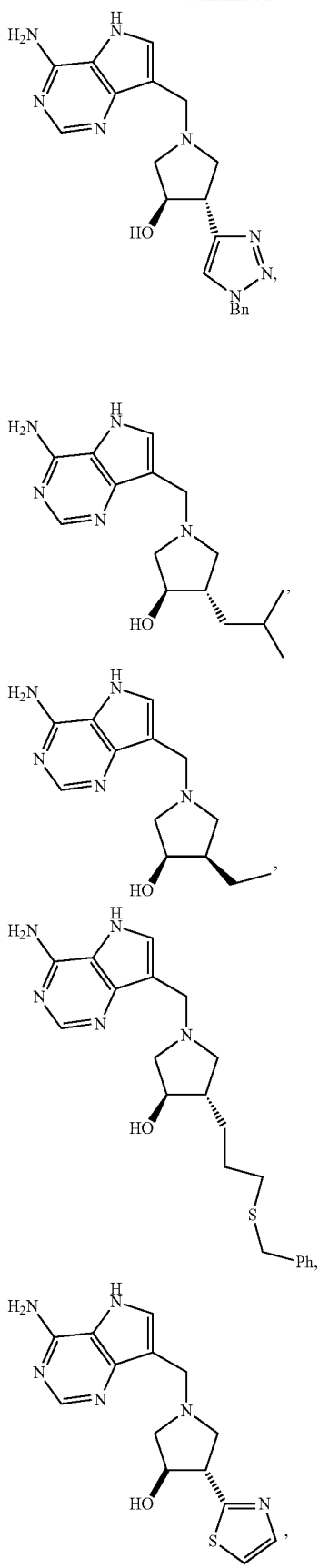

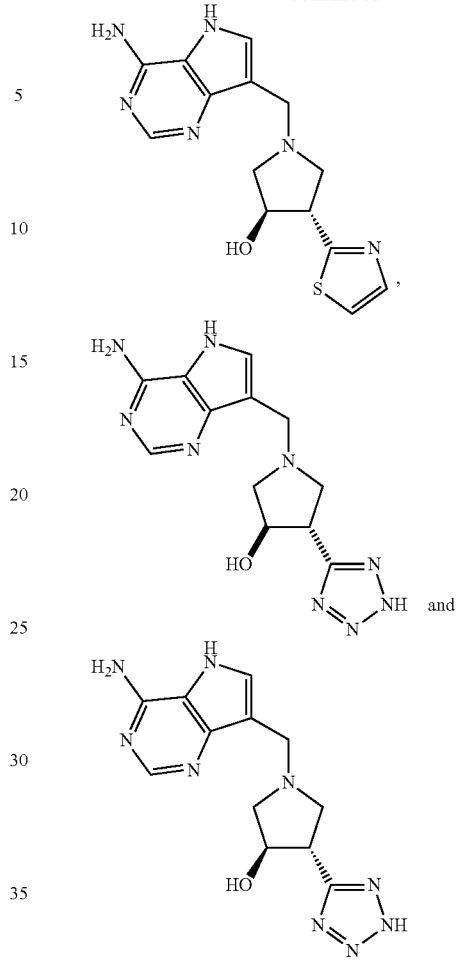

or a tautomer thereof, or a pharmaceutically acceptable salt thereof, or an ester prodrug form thereof.

In another aspect the invention, provides a composition comprising a pharmaceutically effective amount of a compound of formula (I), (Ia), (Ib) or (Ic) and optionally a pharmaceutically acceptable carrier.

In another aspect the invention provides a pharmaceutical composition comprising a pharmaceutically effective amount of a compound of formula (I), (Ia), (Ib) or (Ic) and optionally a pharmaceutically acceptable carrier.

In another aspect the invention provides a compound of formula (I), (Ia), (Ib) or (Ic) in combination with at least one other compound, e.g. a second drug compound. The other compound may be, for example, methylthioadenosine or an anti-bacterial agent or an anti-cancer agent.

In another aspect the invention provides the use of a compound of formula (I), (Ia), (Ib) or (Ic) for inhibiting 5'-methylthioadenosine phosphorylase or 5'-methylthioadenosine nucleosidase.

In another aspect the invention provides the use of a compound of formula (I), (Ia), (Ib) or (Ic) as a medicament.

In another aspect the invention provides the use of a compound of formula (I), (Ia), (Ib) or (Ic) for treating or preventing a disease or condition in which it is desirable to inhibit 5'-methylthioadenosine phosphorylase or 5'-methylthioadenosine nucleosidase.

In another aspect the invention provides the use of a compound of formula (I), (Ia), (Ib) or (Ic) for treating or preventing a bacterial infection or cancer.

In another aspect the invention provides the use of a pharmaceutical composition comprising a pharmaceutically effective amount of a compound of formula (I), (Ia), (Ib) or (Ic) for treating or preventing a disease or condition in which it is desirable to inhibit 5'-methylthioadenosine phosphorylase or 5'-methylthioadenosine nucleosidase.

In another aspect the invention provides the use of a pharmaceutical composition comprising a pharmaceutically effective amount of a compound of formula (I), (Ia), (Ib) or (Ic) for treating or preventing a bacterial infection or cancer.

In another aspect the invention provides the use of a compound of formula (I), (Ia), (Ib) or (Ic) for use in the manufacture of a medicament.

In another aspect the invention provides a pharmaceutical composition for treating or preventing a disease or condition in which it is desirable to inhibit 5'-methylthioadenosine phosphorylase or 5'-methylthioadenosine nucleosidase, comprising a compound of formula (I), (Ia), (Ib) or (Ic).

In another aspect the invention provides a pharmaceutical composition for treating or preventing a bacterial infection or cancer, comprising a compound of formula (I), (Ia), (Ib) or (Ic).

In another aspect the invention provides the use of a compound of formula (I), (Ia), (Ib) or (Ic) in the manufacture of a medicament for the treatment or prevention of a disease or condition in which it is desirable to inhibit 5'-methylthioadenosine phosphorylase or 5'-methylthioadenosine nucleosidase.

In another aspect the invention provides a method of treating or preventing a disease or condition in which it is desirable to inhibit 5'-methylthioadenosine phosphorylase or 5'-methylthioadenosine nucleosidase comprising administering a pharmaceutically effective amount of a compound of formula (I), (Ia), (Ib) or (Ic) to a patient requiring treatment.

In another aspect the invention provides a method of treating or preventing a bacterial infection or cancer comprising administering a pharmaceutically effective amount of a compound of formula (I), (Ia), (Ib) or (Ic) to a patient requiring treatment.

In another aspect the invention provides the use of a compound of formula (I), (Ia), (Ib) or (Ic) in combination with at least one other compound, e.g. a second drug compound, e.g. methylthioadenosine or an anti-bacterial agent or an anti-cancer agent, for treating or preventing a disease or condition in which it is desirable to inhibit 5'-methylthioadenosine phosphorylase or 5'-methylthioadenosine nucleosidase (e.g. a bacterial infection or cancer). In another aspect the invention provides a method of treating or preventing a disease or condition in which it is desirable to inhibit 5'-methylthioadenosine phosphorylase or 5'-methylthioadenosine nucleosidase (e.g. a bacterial infection or cancer) comprising administering a pharmaceutically effective amount of a compound of formula (I), (Ia), (Ib) or (Ic) in combination with at least one other compound, e.g. a second drug compound, e.g. methylthioadenosine or an anti-bacterial agent or an anti-cancer agent. The compound of formula (I), (Ia), (Ib) or (Ic) and the other compound may be administered separately, simultaneously or sequentially.

The diseases or conditions include cancer, e.g. prostate cancer or head and neck cancer and bacterial infections, e.g. those caused by *Vibrio cholerae, Escherichia coli, Streptococcus pneumoniae, Neisseria meningitidis, Klebsiella pneumoniae, Staphylococcus aureus*, or *Helicobacter pylori*.

The compound of formula (I), (Ia), (Ib) or (Ic) may be selected from compounds (i) to (xii) as defined above.

Compounds of formulae (I), (Ia), (Ib) and (Ic) are hereinafter described as "compounds of the invention". A compound of the invention includes a compound in any form, e.g. in free form or in the form of a salt or a solvate.

DETAILED DESCRIPTION

Definitions

The term "alkyl" means any saturated hydrocarbon radical having up to 30 carbon atoms and includes any $C_1$-$C_{25}$, $C_1$-$C_{20}$, $C_1$-$C_{10}$, or $C_1$-$C_6$ alkyl group, and is intended to include both straight- and branched-chain alkyl groups. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group.

The term "lower alkyl" means any saturated hydrocarbon radical having from 1 to 6 carbon atoms and is intended to include both straight- and branched-chain alkyl groups.

Any alkyl group may optionally be substituted with one or more substituents selected from the group consisting of substituted with one or more substituents selected from the group consisting hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy, or alkoxy groups; where $R^2$ and $R^3$ are independently selected from alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, or $NR^2R^3$ groups, where each alkylthio, arylthio and aralkylthio group is optionally substituted with one or more alkyl, halogen, amino, hydroxy, or alkoxy groups.

The term "cycloalkyl" means means a saturated or partially saturated non-aromatic carbocyclic group, having preferably from 3 to 8 ring carbon atoms, and includes heterocycles where one or more of the ring carbon atoms is replaced with one or more heteroatoms, e.g. nitrogen, oxygen or sulfur. Examples of cycloalkyl groups include, but are not limited to: cyclopropyl group, cyclobutyl group, cyclopentyl group, cyclohexyl group, cycloheptyl group, cyclooctyl group, pyrrolidinyl group, pyrrolinyl group, pyrazolidinyl group, aziridinyl group, thiiranyl group, 1,2-dithietanyl group, morpholinyl group, furanyl group, pyranyl group, thiophenyl group, isoxazolyl group, furazanyl group, tetrahydrofuranyl group, thietanyl group, piperidinyl group, azetidinyl group, oxiranyl group, epoxide group or thiacyclohexyl group.

Any cycloalkyl group may optionally be substituted with one or more substituents selected from the group consisting of substituted with one or more substituents selected from the group consisting hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy, or alkoxy groups; where $R^2$ and $R^3$ are independently selected from alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, or $NR^2R^3$ groups, where each alkylthio, arylthio and aralkylthio group is optionally substituted with one or more alkyl, halogen, amino, hydroxy, or alkoxy groups.

The term "alkenyl" means any hydrocarbon radical having at least one double bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkenyl group, and is intended to include both straight- and branched-chain alkenyl groups. Examples of alkenyl groups include: ethenyl group, n-propenyl group, iso-propenyl group, n-butenyl group, iso-butenyl group, sec-butenyl group, t-butenyl group, n-pentenyl group, 1,1-dimethylpropenyl group, 1,2-dimethylpropenyl group, 2,2-dimethylpropenyl group, 1-ethylpropenyl group, 2-ethylpropenyl group, n-hexenyl group and 1-methyl-2-ethylpropenyl group.

The term "lower alkenyl" means any hydrocarbon radical having at least one double bond, and having from 2 to 6 carbon atoms, and is intended to include both straight- and branched-chain alkenyl groups.

Any alkenyl group may optionally be substituted with one or more substituents selected from the group consisting of substituted with one or more substituents selected from the group consisting hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy, or alkoxy groups; where $R^2$ and $R^3$ are independently selected from alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, or $NR^2R^3$ groups, where each alkylthio, arylthio and aralkylthio group is optionally substituted with one or more alkyl, halogen, amino, hydroxy, or alkoxy groups.

The term "alkynyl" means any hydrocarbon radical having at least one triple bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkynyl group, and is intended to include both straight- and branched-chain alkynyl groups. The same terminology applies to the non-aromatic moiety of an aralkynyl radical. Examples of alkynyl groups include: ethynyl group, n-propynyl group, iso-propynyl group, n-butynyl group, iso-butynyl group, sec-butynyl group, t-butynyl group, n-pentynyl group, 1,1-dimethylpropynyl group, 1,2-dimethylpropynyl group, 2,2-dimethylpropynyl group, 1-ethylpropynyl group, 2-ethylpropynyl group, n-hexynyl group, and 1-methyl-2-ethylpropynyl group.

The term "lower alkynyl" means any hydrocarbon radical having at least one triple bond, and having from 2 to 6 carbon atoms, and is intended to include both straight- and branched-chain alkynyl groups.

Any alkynyl group may optionally be substituted with one or more substituents selected from the group consisting of substituted with one or more substituents selected from the group consisting hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy, or alkoxy groups; where $R^2$ and $R^3$ are independently selected from alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, or $NR^2R^3$ groups, where each alkylthio, arylthio and aralkylthio group is optionally substituted with one or more alkyl, halogen, amino, hydroxy, or alkoxy groups.

The term "aryl" means an aromatic radical having 4 to 18 carbon atoms and includes heteroaromatic radicals. Examples include monocyclic groups, as well as fused groups such as bicyclic groups and tricyclic groups. Some examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

Any aryl group may optionally be substituted with one or more substituents selected from the group consisting of substituted with one or more substituents selected from the group consisting hydroxy, alkoxy, cycloalkyl, thiol, alkylthio, arylthio, aralkylthio, halogen, carboxylic acid, carboxylate alkyl ester, nitro, cyano, thiazole or $NR^2R^3$ group, where each alkylthio, arylthio and aralkylthio group is optionally substituted with one or more alkyl, halogen, amino, hydroxy, or alkoxy groups; where $R^2$ and $R^3$ are independently selected from alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, or $NR^2R^3$ groups, where each alkylthio, arylthio and aralkylthio group is optionally substituted with one or more alkyl, halogen, amino, hydroxy, or alkoxy groups.

The term "halogen" includes fluorine, chlorine, bromine and iodine.

The term "prodrug" as used herein means a pharmacologically acceptable derivative of the compounds of formulae (I), (Ia), (Ib) and (Ic), such that an in vivo biotransformation of the derivative gives the compound as defined in formulae (I), (Ia), (Ib) and (Ic). Prodrugs of compounds of formulae (I), (Ia), (Ib) and (Ic) may be prepared by modifying functional groups present in the compounds in such a way that the modifications are cleaved in vivo to give the parent compound. Typically, prodrugs of the compounds of formulae (I), (Ia), (Ib) and (Ic) will be ester prodrug forms.

An ester prodrug form of a compound of formula (I), (Ia), (Ib) or (Ic) may be advantageous to enhance bioavailability. Examples of suitable prodrugs include esters of a compound of formula (I), (Ia), (Ib) or (Ic) formed between the 3-hydroxy group on the pyrrolidine ring of compounds of formula (I), (Ia), (Ib) or (Ic) and the carboxylic acid moiety of an alkylcarboxylic acid, an aralkylcarboxylic acid, an aryl carboxylic acid, an amino acid, a dipeptide, a tripeptide or one of the carboxylic acids of a dicarboxylic acid. An ester prodrug can be metabolised in the individual, for example, through cleavage by endogenous esterases, to yield the pharmaceutically active species (e.g. the compound of formula (I), (Ia), (Ib) or (Ic)) and the carboxylic acid.

The term "pharmaceutically acceptable salts" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

The term "protecting group" means a group that selectively protects an organic functional group, temporarily masking the chemistry of that functional group and allowing other sites in the molecule to be manipulated without affecting the functional group. Suitable protecting groups are known to those skilled in the art and are described, for example, in *Protective Groups in Organic Synthesis* (3$^{rd}$ Ed.), T. W. Greene and P. G. M. Wuts, John Wiley & Sons Inc (1999). Examples of protecting groups include, but are not limited to: t-butoxycarbonyl group, carbobenzyloxy group, sulfonamide-based protecting groups, L-menthyloxycarbonyl group or mandelate group.

The term "patient" includes human and non-human animals.

The terms "treatment", "treating" and the like include the reduction or alleviation of one or more symptom associated with the disease or disorder, for example, for bacterial infections this can mean reduction in the bacterial load and/or prevention of infection, and/or reduction in toxin production.

The terms "preventing", "prevention" and the like include the prevention of one or more symptom associated with the disease or disorder.

It will be appreciated that the compounds of formulae (I), (Ia), (Ib) and (Ic) can exist as tautomers. For example, where substituent D is a hydroxy group, the compounds can exist as keto or enol forms. The scope of this invention is intended to cover all possible tautomeric forms of the compounds.

It will be appreciated that the compounds of formula (I) can exist as cis and trans isomers. For example, the substituents X and OH on the hydroxypyrrolidine ring can be in either the cis or the trans orientation. The scope of this invention is intended to cover all such isomeric forms of the compounds.

It will also be appreciated that the compounds of formulae (I), (Ia), (Ib) and (Ic) can exist in the form of optical isomers, racemates and diastereomers. The scope of this invention is intended to cover all possible stereoisomeric forms of the compounds of formulae (I), (Ia), (Ib) and (Ic). For example, the hydroxypyrrolidine ring carbon atoms to which the substituents X and OH are attached are asymmetric carbons and may be in the R- or S-configuration. Certain compounds of the invention have stereochemistry with respect to positions 3 and 4 of the pyrrolidine ring that is the same as the stereochemistry of Compound 20 of Example 12. Other compounds of the invention have stereochemistry with respect to positions 3 and 4 of pyrrolidine ring that is the opposite to the stereochemistry of Compound 20 of Example 12.

As used herein, the structural formulae showing the "wedge" notation, e.g.:

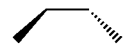

are intended to represent pure enantiomeric forms of a trans isomer.

The structural formulae showing the "rectangular" notation, e.g.:

are intended to represent racemic mixtures of trans isomers.

Similarly, the structural formulae showing the "wedge" notation, e.g.:

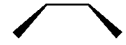

are intended to represent pure enantiomeric forms of a cis isomer.

The structural formulae showing the "rectangular" notation, e.g.:

are intended to represent racemic mixtures of cis isomers.

The Compounds of the Invention

The compounds of the invention, particularly those exemplified, are inhibitors of MTAP and/or MTAN and are useful as pharmaceuticals, particularly for the treatment or prevention of diseases or conditions in which it is desirable to inhibit 5'-methylthioadenosine phosphorylase or 5'-methylthioadenosine nucleosidase, e.g. cancers or bacterial infections.

The compounds of the invention are useful in both free base form and in the form of salts and/or solvates.

Advantageously, certain compounds of the invention, e.g. those which do not contain sulfur atoms, are indicated to have improved biological half lives.

Also advantageously, certain compounds of the invention (e.g. the benzylthiopropyl compound of Example 16, triazole compound of Example 15 and the benzyl-triazole compound of Example 14) show some selectivity for bacterial MTAN.

The active compounds may be administered to a patient by a variety of routes, including orally, parenterally, by inhalation spray, topically, rectally, nasally, buccally or via an implanted reservoir. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams. The specific dosage required for any particular patient will depend upon a variety of factors, including the patient's age, body weight, general health, sex, etc.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

Synthesis of the Compounds of the Invention

The compounds of the invention may be prepared by a variety of different methods. The following are representative non-limiting examples.

General Procedure 1: Synthesis of 1-(9-deaza-adenin-9-ylmethyl)-3-hydroxypyrrolidines (1)

In accordance with General Procedure 1 (Scheme 1), the trans-3-hydroxypyrrolidine starting material 11 is prepared in 5 steps from commercially available diallylamine. The nitrogen of the diallylamine is protected with a suitable protecting group such as t-butoxycarbonyl group, carbobenzyloxy group, a sulfonamide-based protecting group, e.g. toluenesulfonamide group or 2-nitrophenylsulfonamide group, or a chiral auxiliary (which can be employed if it is desired to resolve the pyrrolidine), e.g. 1-(R)-1-(naphthyl)ethylaminocarbonyl group, L-menthyloxycarbonyl group or mandelate group. Compounds of formulae (I), (Ia), (Ib) and (Ic) may be prepared from 3-hydroxypyrrolidine as shown in step f of Scheme 1 and as described in General Procedures 2, 3, 4 and 5 below. Chiral compounds of formulae (I), (Ia), (Ib) and (Ic) may be prepared by resolving racemic mixtures of the final product 1, using standard techniques for example, by crystallisation with a chiral acid (see, e.g., Principles and Applications of Stereochemistry by M. North (Bangor University). Stanley Thornes: Cheltenham, UK 1998), or by using a chiral hydroxypyrrolidine starting material. Such chiral starting materials can be obtained by resolving racemic mixtures of the hydroxypyrrolidine 11.

Racemic amines such as 11 can be resolved in a various ways. For example, such racemic amines can be resolved by crystallisation with a chiral acid (see, e.g., Principles and Applications of Stereochemistry by M. North (Bangor University). Stanley Thornes: Cheltenham, UK 1998). Alternatively, racemic secondary amines such as 11 can be resolved by separation of diastereomeric carbamate or urea derivatives, e.g. those made by reaction with a chiral carbamoylation reagent such a L-menthyl chloroformate (R. L. Eisenberg, The Chemical Educator, 3 (1998) 1-17) or with chiral isocyantes such as 1-(R)-1-(naphthyl)ethyl isocyanate (Handbook of Reagents for Organic Synthesis: Chiral reagents for asymmetric synthesis, Leo A. Paquette, Chichester; Hoboken, N.J.: Wiley, 2003).

Formation of pyrrolidines 4 and 8 can be achieved in a various ways, for example by treatment of 1,4-dichlorobutene with a suitable amine (see, e.g.: Organic Process Research and Development, 2009, 13, 638-640). Formation of expoxides 5 and 9 can also be achieved with trifluoroacetone and OXONE (see, e.g., Bioorganic & Medicinal Chemistry Letters, 2005, vol. 15, no. 21, 4770-4773). Opening of the epoxide may also be achieved with organolithium/copper species, for example $R_2CuLi$, where R=Me, n-Bu, n-Oct, Ph (see, e.g., Eur. J. Org. Chem, 2009, 2474-2489).

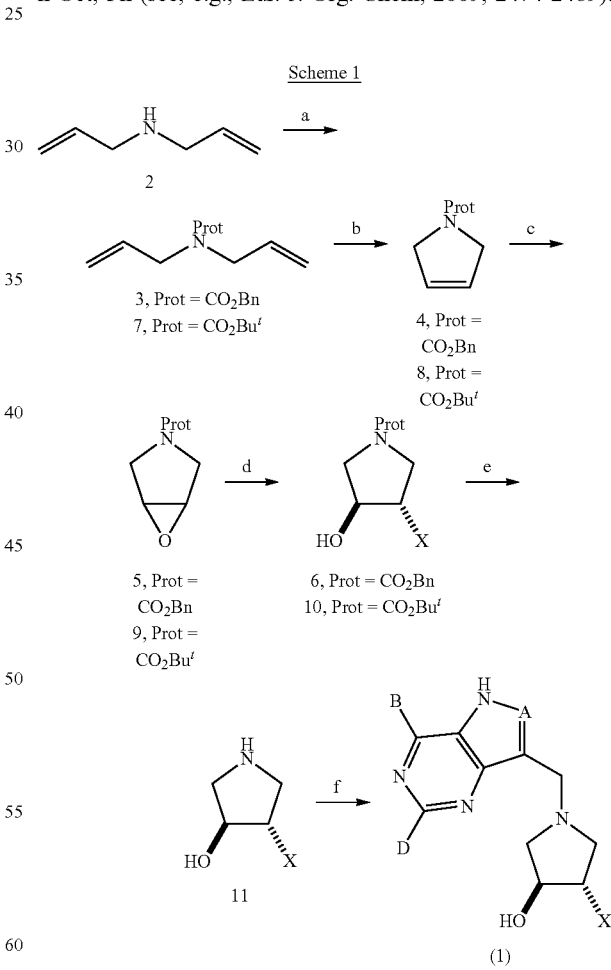

Scheme 1

Reagents and Conditions: (a) $(Boc)_2O$, MeOH or Cbz-Cl, $Et_3N$, $CH_2Cl_2$; (b) Grubb's $1^{st}$ Generation catalyst; (c) m-CBPA, DCM, 50° C., or (i) NBS, $DMSO:H_2O$, (ii) NaOH, MeOH; (d) XMgHal, $CuBr.DMS$, THF, −30° C.; or trimethysilylacetylene, n-BuLi, $BF_3.OEt_2$, THF, −78° C. (e)

Pd/C, MeOH, H$_2$ or HCl, MeOH; (f) formaldehyde, 1,4-dioxane, H$_2$O (Hal=halogen).

General Procedure 2—Mannich Reaction

Compounds of formulae (I), (Ia), (Ib) and (Ic) may be prepared by reacting a pyrrolidine of formula (II) for formula (III) with formaldehyde and a 9-deazapurine (e.g. 9-deazaadenine) in a Mannich reaction as shown above in step f of Scheme 1, and below in Schemes 2 and 2a. The Mannich reaction is followed by deprotection, if necessary. Compounds of formulae (I), (Ia), (Ib) and (Ic) may be prepared in this way, as described in WO 2004/069856.

Scheme 2: Racemic Pyrrolidine (II)

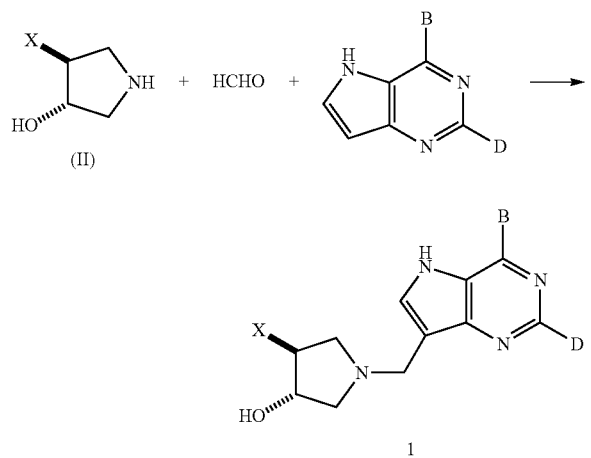

Scheme 2a: Chiral Pyrrolidine (III)

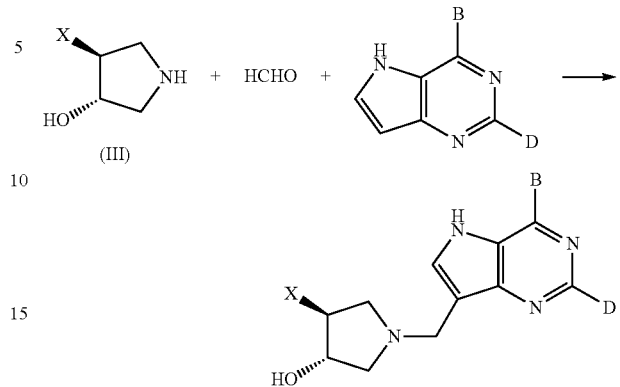

General Procedure 3—Reductive Amination

Alternatively, compounds of formulae (I), (Ia), (Ib) and (Ic) may be prepared by reductive amination of an aldehyde with the racemic pyrrolidine of formula (II) (as shown in Scheme 3) or analogously with the chiral pyrrolidine of formula (III). This reaction can be effected using reagents such as, but not limited to, NaBH$_3$CN or Na(OAc)$_3$BH. Conversion of the 4-tert-butoxy- to 4-amino-5H-pyrrolo-[3,2-d]-pyrimidine may be effected as shown. Suitable deprotection steps follow. Suitable protected aldehydes are known (e.g. *J. Org. Chem.* 2004, 69, 2217-2220).

Scheme 3

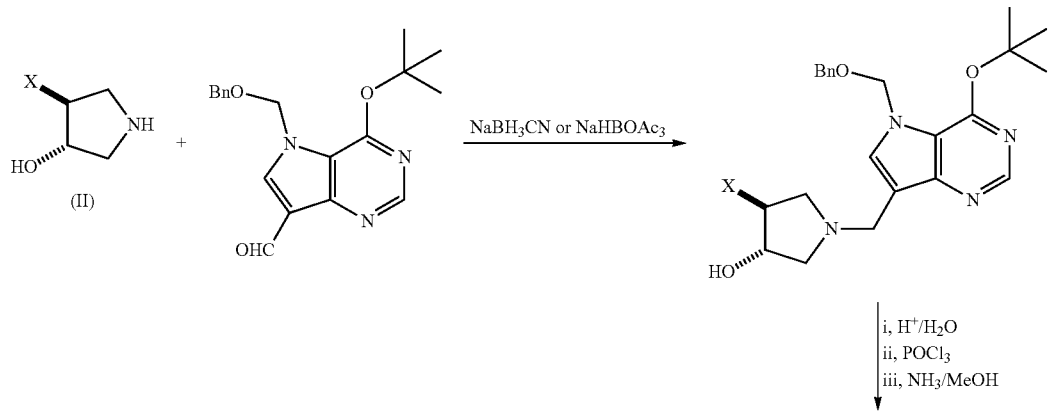

i, H$^+$/H$_2$O
ii, POCl$_3$
iii, NH$_3$/MeOH

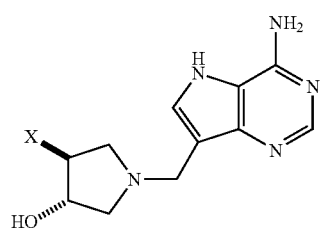

Reductive amination of the aldehyde of 4-choro compounds followed by conversion of the 4-chloro to the 4-amino can be employed, as shown in Scheme 4 below. An example is the preparation and reductive amination of 5-(benzyloxymethyl)-4-chloro-5H-pyrrolo[3,2-d]pyrimidine-7-carbaldehyde as shown.

(e.g. as shown in Scheme 5 below). Such chiral hydroxypyrrolidines and methods for their synthesis are known, e.g. compound 12 can be prepared as described in WO 2005/118532. The enantiomer of 12 can also be prepared as described in WO 2005/118532. It will be clear to the skilled person that either of these trans enantiomers can be used as Scheme 4

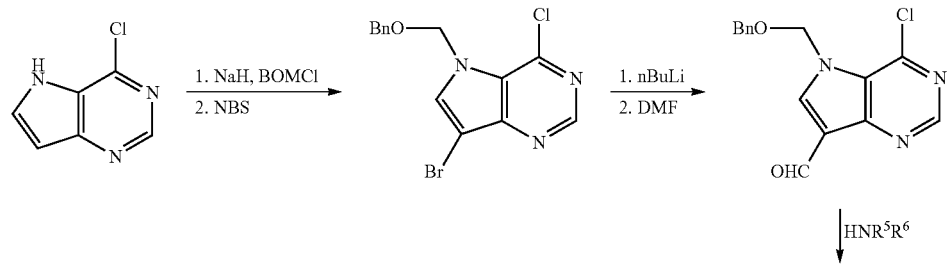

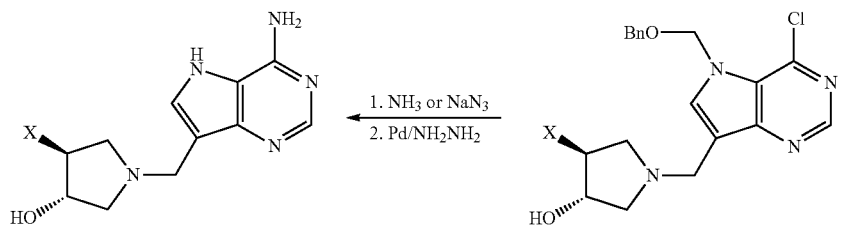

The 3-hydroxypyrrolidines of formulae (II) and (III) may also be prepared by a number of methods, such as those described in Hansen and Bols, 1-Azaribofuranoside Analogues as Designed Inhibitors of Purine Nucleoside Phosphorylase. Synthesis and Biological Evaluation. *Acta. Chem. Scand.* 1998, 52, 1214-22; and Kamal et al., Chemoenzymatic synthesis of (3R,4S)- and (3S,4R)-3-methoxy-4-methylaminopyrrolydine. Tetrahedron Asymmetry 2008, 17, 2876-83.

General Procedure 4—Synthesis of Chiral Compounds of the Invention

Chiral compounds of the invention may also be synthesized using a chiral hydroxypyrrolidine starting material starting material, and the procedure as shown in Scheme 5 is applicable for both trans enantiomers. Similarly, it will be clear to the skilled person that the cis isomers of the compound 12 can be synthesized (see M. Godskesen and I Lundt Tetrahedron Letters 1998, 39, 5841) and these can be used as starting materials for preparing compounds of formula (I) where the OH and the X substituents of the pyrrolidine ring are cis to one another.

Oxidation of the alcohol 15 to aldehyde 16 may also achieved using the Swern oxidation.

Scheme 5

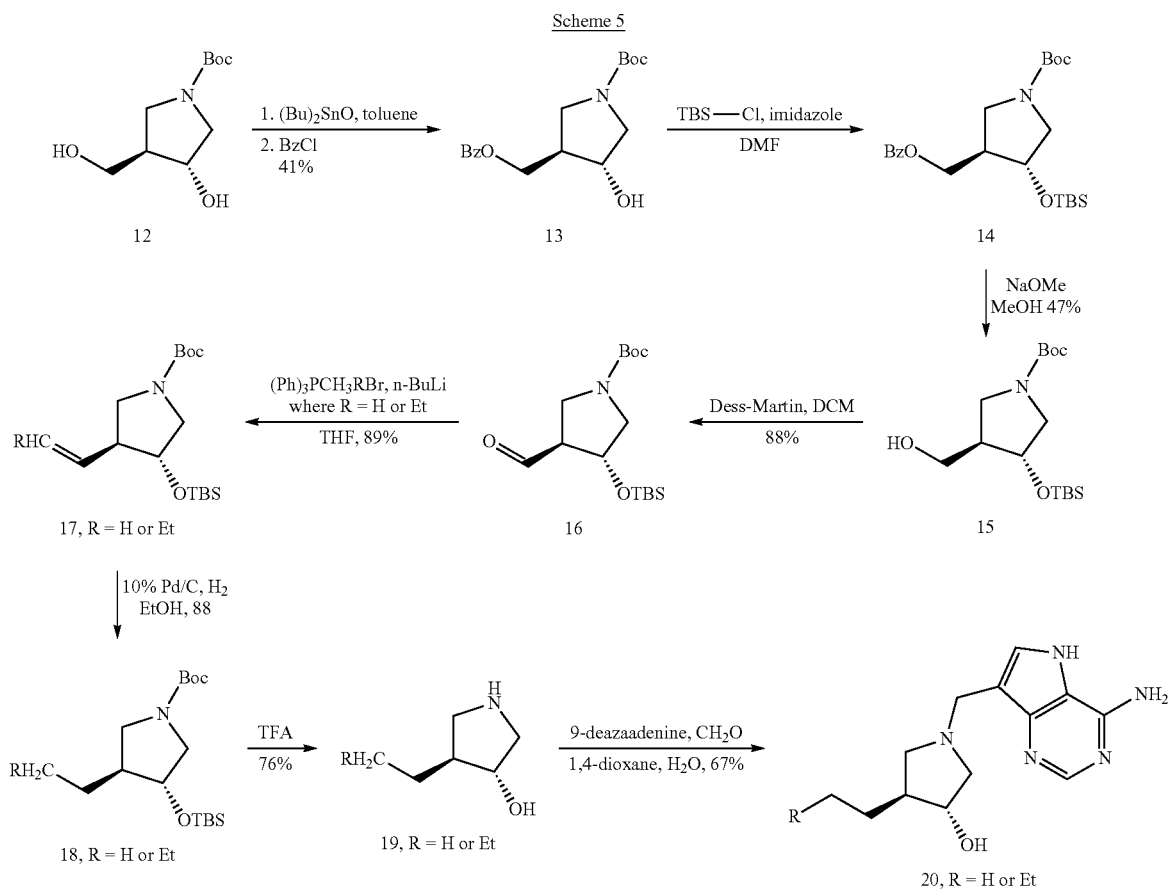

General Procedure 5—Synthesis of Triazole Derivatives

Compounds of formula (I), (Ia), (Ib) or (Ic) where X is an optionally substituted triazolyl or triazolylmethyl group can be prepared as shown in Scheme 6.

Scheme 6

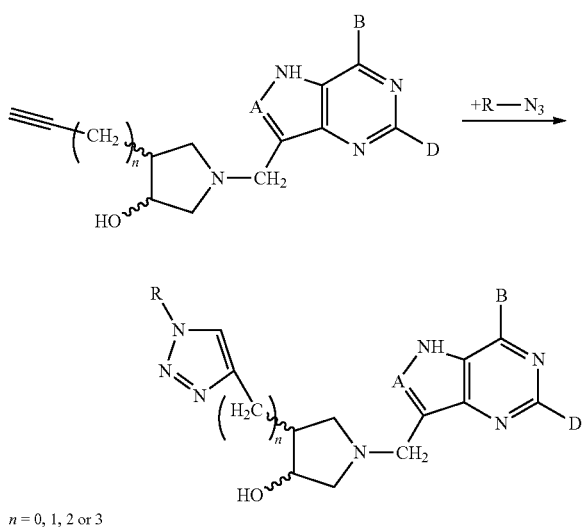

n = 0, 1, 2 or 3

Thus, a compound of formula (I), (Ia), (Ib) or (Ic) where X is an ethynyl or a propyn-3-yl group may be reacted with an organic azide in the presence of a Cu catalyst, in a Click reaction (H. C. Kolb, M. G. Finn and K. B. Sharpless, Angewandte Chemie International Edition 40 (2001) 2004-2021). The triazole may be substituted (the R group in Scheme 6) with aryl group, e.g. phenyl; alkyl group, e.g. a lower alkyl group, e.g. propyl group, which may optionally be substituted with one or more substituents selected from aryl, hydroxyl, alkoxy; or cycloalkyl group.

Those skilled in the art will appreciate that it is also possible to synthesise the triazolyl- or triazolylmethyl-pyrrolidine moiety separately and then couple this to the base using the Mannich reaction (e.g. as described in General Procedure 2) to give the desired product. This procedure is described in Scheme 7. Although Scheme 7 shows the reaction with an X=ethynyl pyrrolidine starting material, the skilled person will appreciate that an X=propyn-3-yl pyrrolidine starting material can also be used. Selective removal of the TMS group from the ethynyl (or propyn-3-yl) pyrrolidine with tetrabutylammonium fluoride gives the desilylated ethynyl pyrrolidine which can be reacted with the appropriate azide (e.g. benzyl azide for an N-benzyl substituted triazolyl species) under Sharpless CuAAC conditions, to give the N-substituted triazol-4-ylpyrrolidine. Removal of the protecting group gives a free pyrrolidine which can be coupled to an appropriate base using the standard Mannich reaction Scheme 7
Scheme 8
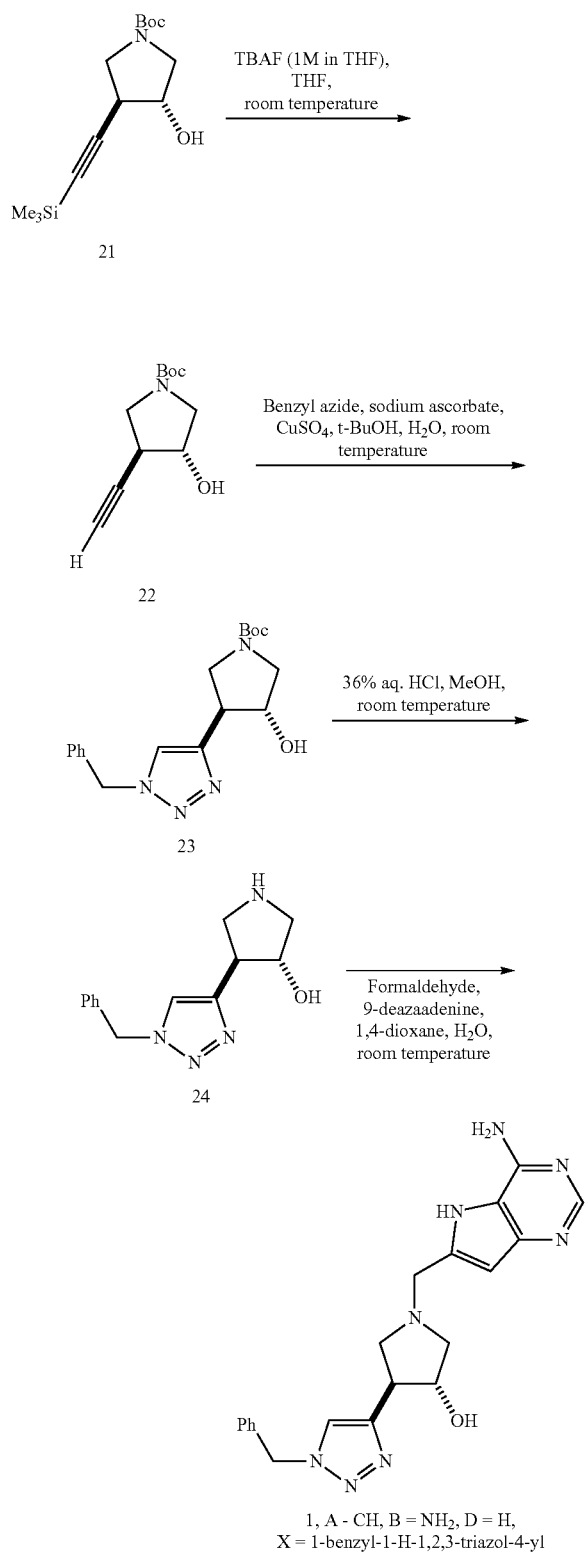
Alternatively, compounds of formula (I), (Ia), (Ib) or (Ic) where X is a triazolyl group which is linked to the pyrrolidine moiety via a 1,2,3-triazol-1-yl ring nitrogen can be prepared as shown in Scheme 8.
Thus, the epoxide-pyrrolidine starting material undergoes ring opening with sodium azide, as reported by Tsuzuki et al. ((Tsuzuki, Y.; Chiba, K.; Mizuno, K.; Tomita, K.; Suzuki, K.

Practical Synthesis of (3S, 4S)-3-methoxy-4-methylpyrrolidine. *Tetrahedron: Asymmetry* 2002, 12, 2989-2997). The resulting azide and trimethylsilylacetylene are heated under reflux in toluene. The crude mixture is treated with tetrabutylammonium fluoride to give the TMS-triazole and the desired desilylated triazole in good yield. Removal of the nitrogen protecting group can be achieved in the presence of acid/alcohol, e.g. HCl/MeOH. The thus obtained pyrrolidine is reacted with the appropriate base using the Mannich reaction, to afford the desired compound.

General Procedure 6—Synthesis of Substituted Alkyl Derivatives

Compounds of formula (I), (Ia), (Ib) or (Ic) where X is an alkyl group substituted with an aralkylthio, an arylthio or an alkylthio group can be prepared as shown in Scheme 9, using the thiol-ene "click reaction" (Becer, C. R., Hoogenboom, R., Schubert, U. S. Click Chemistry beyond Metal-Catalyzed Cycloaddition. Angew. *Chem. Int. Ed.* 2009, 48, 4900-4908; Heidecke, C. D.; Lindhorst, T. K. Iterative Synthesis of Spacered Glycodendrons as Oligomannoside Mimetics and Evaluation of Their Antiadhesive Properties. *Chem. Eur. J.* 2007, 13, 9056-9067).

the appropriate base in a Mannich reaction (e.g. as described in General Procedure 2) to give the desired product.

Abbreviations

NMR nuclear magnetic resonance
tlc thin layer chromatography
MS mass spectroscopy
Boc t-butoxycarbonyl
NBS N-bromosuccinamide
DMSO dimethylsulfoxide
DCM dichloromethane
DMS dimethylsulfide

EXAMPLES

The following examples further illustrate the invention. It is to be appreciated that the invention is not limited to the examples.

General Methods

Anhydrous solvents are obtained commercially. Air sensitive reactions are carried out under argon. Organic solutions are dried over MgSO$_4$ and the solvents are evaporated under reduced pressure. Chromatography solvents are dis-

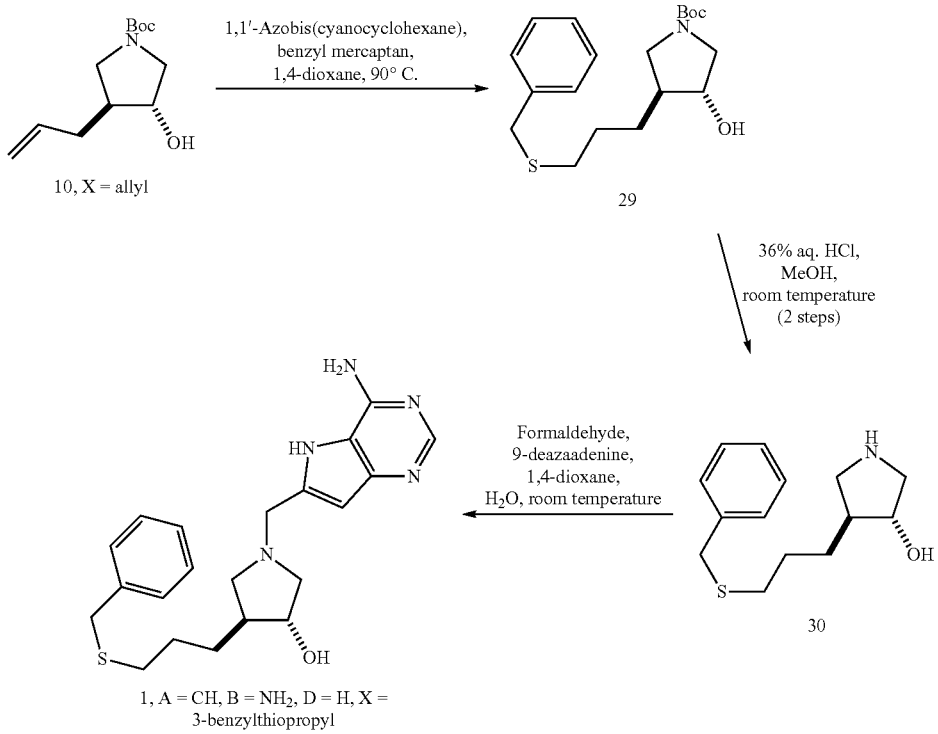

Scheme 9

The allyl pyrrolidine can be synthesised as described in Example 6.1. Reaction of this pyrrolidine intermediate with a suitable mercaptan, such as an aralkyl mercaptan (e.g. benzyl mercaptan), an alkyl mercaptan (e.g. methyl mercaptan, ethyl mercaptan, propyl mercaptan), a cycloalkyl mercaptan (e.g. cyclohexyl mercaptan) or an aryl mercaptan (e.g phenyl mercaptan, tolyl mercaptan) and 1,1'-azobis(cyanocyclohexane) in 1,4-dioxane at 90° C. gives the protected pyrrolidine, which can then be deprotected and reacted with tilled prior to use. Thin layer chromatography (tlc) is performed on glass or aluminium sheets coated with 60 F254 silica. Organic compounds are visualised under UV light or by use of a dip of cerium(IV) sulfate (0.2%, w/v) and ammonium molybdate (5%) in sulfuric acid (2M), one of I$_2$ (0.2%) and KI (7%) in H$_2$SO$_4$ (M), or 0.1% ninhydrin in EtOH. Flash column chromatography is performed on Scharlau or Merck silica gel 60 (40-60 μm). Optical rotations are recorded on a Perkin-Elmer 241 polarimeter with a path length of 1 dm and are in units of $10^{-1}$ deg cm$^2$ g$^{-1}$;

concentrations are in g/100 mL. NMR spectra are recorded on a Bruker AC300E. Unless otherwise stated, $^1$H NMR spectra at 300 MHz are measured in CDCl$_3$, CD$_3$OD (internal reference Me$_4$Si, δ 0) or D$_2$O (no internal reference), and $^{13}$C NMR spectra at 75.5 MHz are measured in CDCl$_3$ (reference, solvent centre line, δ 77.4), CD$_3$OD (reference, solvent centre line δ 49.5) or D$_2$O (no internal reference). Positive electrospray mass spectra are recorded on a Waters Q-TOF Premier Tandem Mass Spectrometer.

Example 1: (±)-trans-1-[(9-Deaza-adenin-9-yl) methyl]-3-hydroxy-4 phenylpyrrolidine (1, X=phenyl, A=CH, B=NH$_2$, D=H)

Example 1.1: Benzyl Diallylcarbamate (3)

A solution of diallylamine (15 mL, 120 mmol) in CH$_2$Cl$_2$ (150 mL) is cooled to 0° C. and Et$_3$N (23 mL, 160 mmol) then benzyl chloroformate (20 mL, 140 mmol) are added drop-wise. The reaction mixture is slowly allowed to warm to room temperature over 16 h then quenched with water (200 mL). The phases are separated and the aqueous is extracted into CH$_2$Cl$_2$ (3×200 mL). The combined organic phase is washed with brine (200 mL), dried (MgSO$_4$), filtered and concentrated under reduced pressure. Flash chromatography (gradient 2 to 10% EtOAc in petrol) of the residue affords the title compound as a pale yellow oil (25.9 g, 92%). $^1$H NMR (500 MHz, CDCl$_3$): δ=7.35-7.29 (5H, m), 5.77 (2H, br. s), 5.17-5.13 (6H, br. m) and 3.88 ppm (4H, br. s). (Tetrahedron: Asymmetry, 2006, 17, 2876-2883).

Example 1.2: Benzyl 3-pyrroline-1-carboxylate (4)

Grubb's 1$^{st}$ generation catalyst (173 mg, 0.21 mmol) is added to a solution of benzyl diallylcarbamate (6.78 g, 29 mmol) in CH$_2$Cl$_2$ (300 mL). The reaction mixture is stirred for 16 h then further catalyst is added (340 mg, 0.4 mmol). The reaction mixture is stirred for a further 16 h then concentrated under reduced pressure. Flash chromatography (1:9 then 2:8, EtOAc:Petrol) affords the title compound as a yellow oil (5.74 g, 94%). $^1$H NMR (500 MHz, CDCl$_3$): δ=7.39-7.29 (5H, m), 5.82-5.80 (1H, m), 5.77-5.75 (1H, m), 5.17 (2H, s), 4.22-4.18 (4H, m). (Tetrahedron: Asymmetry, 2006, 17, 2876-2883).

Example 1.3: Benzyl 3,4-epoxypyrrolidine-1-carboxylate (5)

NBS (5.47 g, 31 mmol) is added to a solution of olefin 4 (5.02 g, 25 mmol) in DMSO (65 mL) and water (3.4 mL) at 0° C. The reaction mixture is warmed to room temperature, stirred for 1.5 h then further NBS (1.1 g, 6.2 mmol) is added. After stirring for a further 3.5 h the reaction is quenched by the addition of water (150 mL) then extracted into EtOAc (3×150 mL). The combined organic phase is washed with brine (3×100 mL), dried (MgSO$_4$), filtered and concentrated under reduced pressure. The residue is dissolved in MeOH (80 mL), cooled to 0° C. and then an aqueous solution of NaOH (37 mL, 37 mmol, 1 M) is added in one portion. The reaction is warmed to room temperature, stirred for 5 h then the MeOH is removed under reduced pressure. The residue is diluted with water (100 mL) and extracted into EtOAc (3×200 mL). The combined organic phase is washed with brine (200 mL), dried (MgSO$_4$), filtered and concentrated under reduced pressure. Flash chromatography of the residue (3:7 then 4:6, EtOAc: Petrol) affords the title compound as a pale yellow oil (3.69 g, 68% over the 2 steps). $^{13}$C NMR (125 MHz, CDCl$_3$): δ=155.3, 136.6, 128.5, 128.0, 127.9, 67.0, 55.5, 54.9, 47.5 and 47.2 ppm; MS (ESI): 242 ([MNa]$^+$, 100%); HRMS (ESI): found: 242.0791, C$_{12}$H$_{13}$NO$_3$Na ([MNa]$^+$) requires: 242.0793. (Tetrahedron: Asymmetry, 2006, 17, 2876-2883).

Example 1.4: Benzyl (±)-trans-3-hydroxy-4-phenylpyrrolidine-1-carboxylate (6, X=phenyl)

A solution of epoxide 5 (149 mg, 0.68 mmol) and CuBr.SMe$_2$ (30 mg, 0.15 mmol) in THF (5.6 mL) is cooled to −30° C. Phenylmagnesium bromide (1.5 mL, 1.5 mmol, 1 M solution in THF) is added drop-wise over 10 min, keeping the temperature below −25° C. After complete addition, the reaction is allowed to warm to −15° C. over 1 h 30 min then cooled back to −30° C. and further phenylmagnesium bromide is added (1.5 mL, 1.5 mmol, 1 M solution in THF). The reaction mixture is allowed to warm to −20° C. over 1 h then quenched with 10% aqueous solution NH$_4$Cl (20 mL) and EtOAc (20 mL). The mixture is stirred at room temperature for 30 min then the layers are separated. The aqueous phase is extracted into EtOAc (3×20 mL). The combined organic phase is dried (MgSO$_4$), filtered and concentrated under reduced pressure. Flash chromatography of the residue (gradient 3:7 to 1:1, EtOAc:Petrol) affords a mixture of the title compound 6 (X=phenyl) and unreacted epoxide 5 as a pale yellow oil [162 mg, 2:1, 6 (X=phenyl): 5].

Example 1.5: (±)-trans-3-Hydroxy-4-phenylpyrrolidine (11, X=phenyl)

Palladium (25 mg, 0.02 mmol, 10 wt % on carbon) is added to a solution of the above mixture of Cbz-protected amine 6 (X=phenyl) and epoxide 5 (160 mg) in MeOH (12 mL) under Argon. The reaction mixture is placed under a hydrogen atmosphere and stirred for 1 h 15 min, then filtered through Celite and concentrated under reduced pressure. Flash chromatography of the residue (5:4.8:0.2 then 5:4.6: 0.4, CH$_2$Cl$_2$:MeOH:NH$_4$OH) affords the title compound 11 (X=phenyl) as a yellow oil (39 mg, 35%, over 2 steps). $^{13}$C NMR (125 MHz, CD$_3$OD): δ=142.7, 129.7, 128.5, 127.8, 80.0, 55.3, 54.9 and 53.6 ppm; MS (ESI): 164 ([MH]$^+$, 100%); HRMS (ESI): found: 164.1068, C$_{10}$H$_{14}$NO ([MH]$^+$) requires: 164.1075.

Example 1.6: (±)-trans-1-[(9-Deaza-adenin-9-yl) methyl]-3-hydroxy-4-phenylpyrrolidine (1, X=phenyl, A=CH, B=NH$_2$, D=H)

Formaldehyde (35 μL, 0.4 mmol, 37 wt % solution in water) followed by 9-deazaadenine (39 mg, 0.24 mmol) are added to a solution of amine 11 (X=phenyl) (30 mg, 0.22 mmol) in 1,4-dioxane (0.4 mL) and water (0.8 mL). The reaction mixture is stirred at room temperature for 17 h, absorbed on to silica and eluted down a silica column with a gradient of 10% to 20% (7 N NH$_3$ in MeOH) in CH$_2$Cl$_2$. The crude product is collected, concentrated and subject to flash chromatography (5:4.9:0.1 then 5:4.8:0.2, CH$_2$Cl$_2$: MeOH:NH$_4$OH) to afford the title compound 1, (X=phenyl, A=CH, B=NH$_2$, D=H) as a white solid (38 mg, 55%). $^{13}$C NMR (125 MHz, CD$_3$OD): δ=152.1, 151.0, 147.0, 143.6, 130.1, 129.5, 128.6, 127.5, 115.2, 112.6, 79.3, 62.8, 61.2, 54.9 and 49.1 ppm; MS (ESI): 332 ([MNa]$^+$, 100%); HRMS (ESI): found: 332.1490, C$_{17}$H$_{19}$N$_5$O$^{23}$Na ([MNa]$^+$) requires: 332.1487.

Example 2: (±)-trans-4-(Cyclohexylmethyl)-1-[(9-deaza-adenin-9-yl)methyl]-3-hydroxy-pyrrolidine (1, X=cyclohexylmethyl, A=CH, B=NH$_2$, D=H)

Example 2.1: Benzyl (±)-trans-4-(cyclohexylmethyl)-3-hydroxypyrrolidine-1-carboxylate (6, X=cyclohexylmethyl)

A solution of epoxide 5 (243 mg, 1.1 mmol) and CuBr.SMe$_2$ (50 mg, 0.22 mmol) in THF (10 mL) is cooled to −30° C. Cyclohexylmethylmagnesium bromide (11 mL, 5.5 mmol, 0.5 M solution in THF) is added drop-wise over 20 min. After complete addition the reaction is allowed to warm to −25° C. over 30 min then quenched with 10% aqueous solution NH$_4$Cl (20 mL) and EtOAc (20 mL). The mixture is stirred at room temperature for 30 min then the layers are separated. The aqueous phase is extracted into EtOAc (3×30 mL). The combined organic phase is dried (MgSO$_4$), filtered and concentrated under reduced pressure. Flash chromatography of the residue (gradient 2:8 to 4:6; EtOAc: Petrol) affords the title compound 6 (X=cyclohexylmethyl) as an off-white solid (286 mg, 81%).

Example 2.2: (±)-trans-4-(Cyclohexylmethyl)-3-hydroxypyrrolidine (11, X=cyclohexylmethyl)

Palladium (20 mg, 0.02 mmol, 10 wt % on carbon) is added to a solution of Cbz-protected amine 6 (X=cyclohexylmethyl) (286 mg, 0.9 mmol) in MeOH (10 mL) under Argon. The reaction mixture is placed under a hydrogen atmosphere and stirred for 1 h, then further catalyst (20 mg, 0.02 mmol, 10 wt % on carbon) is added. The mixture is stirred under a hydrogen atmosphere for a further 1 h then filtered through Celite and concentrated under reduced pressure. Flash chromatography of the residue (5:4.8:0.2 then 5:4.5:0.5, CH$_2$Cl$_2$:MeOH:NH$_4$OH) affords the title compound 11 (X=cyclohexylmethyl) as an off-white solid (115 mg, 70%). $^{13}$C NMR (125 MHz, CD$_3$OD): δ=78.8, 54.5, 52.1, 46.2, 41.6, 37.4, 35.1, 34.3, 27.7 and 27.4 (×2C) ppm; MS (ESI): 184 ([MH]$^+$, 100%); HRMS (ESI); found: 184.1696, C$_{11}$H$_{22}$NO ([MH]$_+$) requires: 184.1701

Example 2.3: (±)-trans-4-(Cyclohexylmethyl)-1-[(9-deaza-adenin-9-yl)methyl]-3-hydroxypyrrolidine (1, X=cyclohexylmethyl, A=CH, B=NH$_2$, D=H)

Formaldehyde (35 µL, 0.4 mmol, 37 wt % solution in water) followed by 9-deazaadenine (42 mg, 0.31 mmol) are added to a solution of amine 11 (X=cyclohexylmethyl) (51 mg, 0.28 mmol) in 1,4-dioxane (1.5 mL) and water (1.5 mL). The reaction mixture is stirred at room temperature for 67 h, absorbed on to silica and eluted down a silica column with a gradient of 5% to 30% (7 N NH$_3$ in MeOH) in CH$_2$Cl$_2$. The crude product is collected, concentrated and subject to flash chromatography (5:4.9:0.1, CH$_2$Cl$_2$ MeOH:NH$_4$OH) to afford the title compound 1 (X=cyclohexylmethyl, A=CH, B=NH$_2$, D=H) as a pale yellow solid (42 mg, 46%). $^{13}$C NMR (125 MHz, CD$_3$OD): δ=152.1, 151.1, 147.0, 130.1, 115.1, 112.5, 78.1, 62.2, 59.8, 49.1, 45.8, 42.4, 37.4, 35.1, 34.2, 27.7 and 27.4 (2×C) ppm; MS (ESI): 330 ([MH]$^+$, 100%); HRMS (ESI): found: 330.2297, C$_{18}$H$_{28}$N$_5$O ([MH]$^+$), requires: 330.2294

Example 3: (±)-trans-1-[9-Deaza-adenin-9-yl)methyl]-3-hydroxy-4-(prop-1-en-2-yl)pyrrolidine (1, X=prop-1-en-2-yl, A=CH, B=NH$_3$, D=H)

Example 3.1: Benzyl (±)-trans-3-hydroxy-4-(prop-1-en-2-yl)pyrrolidine-1-carboxylate (6, X=prop-1-en-2-yl)

A solution of epoxide 5 (199 mg, 0.91 mmol) and CuBr.SMe$_2$ (26 mg, 0.14 mmol) in THF (12 mL) is cooled to −30° C. Isopropenylmagnesium bromide (10 mL, 5.0 mmol, 0.5 M solution in THF) is added drop-wise over 20 min. After complete addition the reaction is allowed to slowly warm to RT over 66 h then quenched with 10% aqueous solution NH$_4$Cl (50 mL) and EtOAc (50 mL). The mixture is stirred at room temperature for 1.5 h then the layers are separated. The aqueous phase is extracted into EtOAc (3×50 mL). The combined organic phase is dried (MgSO$_4$), filtered and concentrated under reduced pressure. Flash chromatography of the residue (gradient 2:8 to 4:6, EtOAc:Petrol) affords the title compound 6 (X=prop-1-en-2-yl) as a pale yellow oil (173 mg, 73%).

Example 3.2: (±)-trans-3-Hydroxy-4-(prop-1-en-2-yl)pyrrolidine (11, X=prop-1-en-2-yl, A=CH, B=NH$_2$, D=H)

A solution of Cbz-protected amine 6 (X=prop-1-en-2-yl) (170 mg, 0.65 mmol) in KOH (4 mL, 8 mmol, 2 M solution in isopropanol) is heated to reflux for 1.5 h. Further KOH (4 mL, 8 mmol, 2 M solution in isopropanol) is added and the mixture refluxed for a further 2.5 h. The RM is then allowed to cool and absorbed onto silica and eluted down a flash column (5:4.5:0.5, DCM:MeOH:NH$_4$OH) to afford the title compound 11 (X=prop-1-en2-yl, A=CH, B=NH$_2$, D=H) as a pale yellow oil (73 mg, 88%). $^{13}$C NMR (125 MHz, CD$_3$OD): δ=143.4, 113.0, 74.2, 54.0, 52.6, 48.5 and 21.7 ppm; MS (ESI): 128 ([MH]$^+$, 100%); HRMS (ESI): found: 128.1070, C$_7$H$_{14}$NO ([MH]$^+$) requires: 128.1075

Example 3.3: (±)-trans-1-[(9-Deaza-adenin-9-yl)methyl]-3-hydroxy-4-(prop-1-en-2-yl)pyrrolidine (1, X=prop-1-en-2-yl, A=CH, B=NH$_2$, D=H)

Formaldehyde (70 µL, 0.9 mmol, 37 wt % solution in water) followed by 9-deazaadenine (74 mg, 0.55 mmol) are added to a solution of amine 11 (X=prop-1-en-2-yl) (65 mg, 0.51 mmol) in 1,4-dioxane (2.6 mL) and water (2.6 mL). The reaction mixture is stirred at room temperature for 16 h, absorbed on to silica and eluted down a silica column with a gradient of 10% to 30% (7 N NH$_3$ in MeOH) in CH$_2$Cl$_2$. The crude product is collected, concentrated and subject to flash chromatography (5:4.9:0.1, CH$_2$Cl$_2$:MeOH:NH$_4$OH). Further purification is achieved by Prep HPLC to afford the title compound 1 (X=prop-1-en-2-yl, A=CH, B=NH$_2$, D=H) as a pale yellow solid (24 mg, 17%). $^{13}$C NMR (125 MHz, CD$_3$OD): δ=152.1, 151.0, 147.0, 145.8, 130.1, 115.2, 112.6, 111.3, 75.6, 62.6, 57.9, 55.8, 49.9 and 21.2 ppm.

Example 4: (±)-trans-4-Cyclopropyl-1-[(9-deaza-adenin-9-yl)methyl]-3-hydroxypyrrolidine (1, X=cyclopropyl, A=CH, B=NH$_2$, D=H)

Example 4.1: Benzyl (±)-trans-4-Cyclopropyl-3-hydroxypyrrolidine-1-carboxylate (6, X=cyclopropyl)

A solution of epoxide 5 (283 mg, 1.3 mmol) and CuBr.SMe$_2$ (43 mg, 0.21 mmol) in THF (10 mL) is cooled to −30° C. Cyclopropylmagnesium bromide (10 mL, 5.0 mmol, 0.5 M solution in THF) is added drop-wise over 25 min. After complete addition the reaction is allowed to slowly warm to −15° C. over 45 min then quenched with 10% aqueous solution NH$_4$Cl (20 mL) and EtOAc (50 mL). The mixture is stirred at room temperature for 40 min then the layers are separated. The aqueous phase is extracted into EtOAc (3×50 mL). The combined organic phase is dried (MgSO$_4$), filtered and concentrated under reduced pressure. Flash chromatography of the residue (3:7 then 4:6, EtOAc: Petrol) affords the title compound 6 (X=cyclopropyl) as a pale yellow oil (311 mg, 92%).

Example 4.2: (±)-trans-4-Cyclopropyl-3-hydroxy-pyrrolidine (11, X=cyclopropyl)

Palladium (25 mg, 0.02 mmol, 10 wt % on carbon) is added to a solution of Cbz-protected amine 6 (X=cyclopropyl) (310 mg, 1.2 mmol) in MeOH (20 mL) under Argon. The reaction mixture is placed under a hydrogen atmosphere and stirred for 1 h, then filtered through Celite and concentrated under reduced pressure. Flash chromatography of the residue (5:4.6:0.4, CH$_2$Cl$_2$:MeOH: NH$_4$OH) affords the title compound 11 (X=cyclopropyl) as an off-white solid (126 mg, 84%). $^{13}$C NMR (125 MHz, CD$_3$OD): δ=76.4, 52.9, 52.6, 50.0, 13.2, 4.2 and 3.6 ppm; MS (ESI): 127 ([MH]$^+$, 100%); HRMS (ESI): found: 128.1082, C$_7$H$_{14}$NO ([MH]$^+$) requires: 128.1075.

Example 4.3: (±)-trans-4-Cyclopropyl-1-1[(9-deaza-adenin-9-yl)methyl]-3-hydroxypyrrolidine (1, X=cyclopropyl, A=CH, B=NH$_2$, D=H)

Formaldehyde (50 µL, 0.6 mmol, 37 wt % solution in water) followed by 9-deazaadenine (60 mg, 0.45 mmol) are added to a solution of amine 11 (X=cyclopropyl) (51 mg, 0.40 mmol) in 1,4-dioxane (1 mL) and water (1 mL). The reaction mixture is stirred at room temperature for 41 h, absorbed on to silica and eluted down a silica column with a gradient of 5% to 30% (7 N NH$_3$ in MeOH) in CH$_2$Cl$_2$. The crude product is collected, concentrated and subject to flash chromatography (5:4.5:0.5, CH$_2$Cl$_2$:MeOH:NH$_4$OH) to afford the title compound 1 (X=cyclopropyl, A=CH, B=NH$_2$, D=H) as an off-white solid (59 mg, 54%). $^{13}$C NMR (125 MHz, CD$_3$OD): δ=152.1, 151.0, 147.0, 130.1, 115.2, 112.5, 77.4, 62.6, 59.1, 53.6, 49.1, 14.5, 3.8 and 3.5 ppm; MS (ESI): 274 ([MH]$^+$, 100%); HRMS (ESI): found: 274.1666, C$_{14}$H$_{20}$N$_5$O ([MH]$^+$) requires: 274.1668.

Example 5: (±)-trans-1-[(9-Deaza-adenin-9-yl) methyl]-3-hydroxy-4-vinylpyrrolidine (1, X=vinyl, A=CH, B=NH$_3$, D=H)

Example 5.1: tert-Butyl diallylcarbamate (7)

Di-tert-butyl dicarbonate (42.2 g, 193 mmol) is added, portion-wise, to a solution of diallylamine (2) (20 mL, 162 mmol) in methanol (500 mL) at 0° C. After complete addition the reaction mixture is allowed to warm to room temperature, stirred for 1 h then concentrated under reduced pressure. Dry vacuum chromatography of the residue (gradient 0 to 50% EtOAc in Petrol) affords the title compound 7 as a colourless oil (31.9 g, 99%). (Org. Biomol. Chem. 2004, 2, 2418-2420).

Example 5.2: tert-Butyl 3-pyrroline-1-carboxylate (8)

Grubb's 1$^{st}$ generation catalyst (920 mg, 1.1 mmol) is added to a solution of tert-butyl diallylcarbamate 7 (31.9 g, 162 mmol) in CH$_2$Cl$_2$ (370 mL). The reaction mixture is stirred for 17 h then concentrated under reduced pressure. Dry vacuum chromatography of the residue (gradient 0 to 70% EtOAc in Petrol) affords the title compound 8 as a pale yellow oil (19.9 g, 73%). (Org. Biomol. Chem. 2004, 2, 2418-2420).

Example 5.3: tert-butyl 3,4-Epoxypyrrolidine-1-carboxylate (9)

m-CPBA (44.3 g, 180 mmol) is added to a solution of olefin 8 (13.7 g, 81 mmol) in CH$_2$Cl$_2$ (217 mL). The resulting suspension is heated to reflux for 4 h, cooled, filtered then diluted with CH$_2$Cl$_2$ (200 mL). The combined organic phase is washed with a saturated solution of sodium sulfite (2×200 mL), aq. NaHCO$_3$ (2×200 mL) and brine (2×200 mL) then dried (MgSO$_4$), filtered and concentrated under reduced pressure. Flash chromatography of the residue (2:8, EtOAc:Petrol) affords the title compound 9 as a pale yellow oil (9.1 g, 61%). (Acta Chemica Scandinavica 1998, 52, 1214-1222).

Example 5.4: tert-butyl (±)-trans-3-hydroxy-4-vinylpyrrolidine-1-carboxylate (10, X=vinyl)

A solution of epoxide 9 (331 mg, 1.8 mmol) and CuBr.SMe$_2$ (73 mg, 0.35 mmol) in THF (15 mL) is cooled to −30° C. Vinylmagnesium bromide (8 mL, 8.0 mmol, 1 M solution in THF) is added drop-Wise over 15 min. After complete addition, the reaction is allowed to slowly warm to −10° C. over 1 h then quenched with 10% aqueous solution NH$_4$Cl (20 mL) and EtOAc (50 mL). The mixture is stirred at room temperature for 1 h then the layers are separated. The aqueous phase is extracted into EtOAc (3×50 mL). The combined organic phase is dried (MgSO$_4$), filtered and concentrated under reduced pressure to afford the title compound 10 (X=vinyl) (286 mg, 75%). No further purification attempted. (Acta Chemica Scandinavica 1998, 52, 1214-1222).

Example 5.5: (±)-trans-3-Hydroxy-4-vinylpyrrolidine (11, X=vinyl)

Concentrated hydrochloric acid (1 mL) is added to a solution of Boc protected amine 10 (X=vinyl) (286 mg, 1.34 mmol) in MeOH (20 mL). The reaction mixture is concentrated under reduced pressure then azeotroped with MeOH (20 mL) and then toluene (20 mL). Flash chromatography of the residue (5:4.6:0.4, CH$_2$Cl$_2$:MeOH:NH$_4$OH) affords the title compound (11, X=vinyl) as a brown oil (95 mg, 63%). $^{13}$C NMR (125 MHz, CD$_3$OD): δ=139.4, 116.1, 78.3, 54.6, 53.5 and 51.3 ppm; MS (ESI): 114 ([MH]$^+$, 100%); HRMS (ESI): found: 114.0911, C$_6$H$_{12}$NO ([MH]$^+$) requires: 144.0919. (Acta Chemica Scandinavica 1998, 52, 1214-1222).

Example 5.6: (±)-trans-1[(9-Deaza-adenin-9-yl) methyl]-3-hydroxy-4-vinylpyrrolidine (1, X=vinyl, A=CH, B=NH$_2$, D=H)

Formaldehyde (45 µL, 0.56 mmol, 37 wt % solution in water) followed by 9-deazaadenine (61 mg, 0.46 mmol) are added to a solution of amine (11, X=vinyl) (42 mg, 0.37 mmol) in 1,4-dioxane (1 mL) and water (1 mL). The reaction mixture is stirred at room temperature for 17 h, absorbed on to silica and eluted down a silica column with a gradient of 5% to 20% (7 N NH$_3$ in MeOH) in CH$_2$Cl$_2$. The crude product is collected, concentrated and subject to flash chromatography (5:4.5:0.5, CH$_2$Cl$_2$:MeOH:NH$_4$OH) to afford the title compound (1, X=vinyl, A=CH, B=NH$_2$, D=H) as an off-white solid (55 mg, 57%). $^{13}$C NMR (125 MHz, CD$_3$OD): δ=152.1, 151.0, 147.0, 139.7, 130.3, 116.0, 115.2, 112.1, 77.2, 61.9, 58.7, 52.9 and 49.1 ppm; MS (ESI): 260 ([MH]$^+$, 100%); HRMS (ESI): found: 260.1511, C$_{13}$H$_{18}$N$_5$O ([MH]$^+$) requires: 260.1511.

Example 6: (±)-trans-4-Allyl-1-[(9-deaza-adenin-9-yl)methyl]-3-hydroxypyrrolidine (1, X=allyl, A=CH, B=NH$_2$, D=H)

Example 6.1: tert-butyl (±)-trans-4-allyl-3-hydroxy-pyrrolidine-1-carboxylate (10, X=allyl)

A solution of epoxide 9 (227 mg, 1.2 mmol) in ether (2.6 mL) is added drop-wise to a solution of allylmagnesium chloride (1.4 mL, 2.8 mmol, 2 M solution in THF) in ether (4.4 mL) at 0° C. The reaction mixture is stirred at 0° C. for 15 min then warmed to room temperature. After 1.5 h the reaction mixture is quenched by the addition of saturated aqueous solution of NH$_4$Cl (20 mL) and extracted into EtOAc (3×50 mL). The combined organic phase is washed with brine (2×50 mL), dried (MgSO$_4$), filtered and concentrated under reduced pressure. Flash chromatography of the residue (1:9, EtOAc:Petrol) affords the title compound (10, X=allyl) as a pale yellow oil (138 mg, 50%). $^{13}$C NMR (125 MHz, CDCl$_3$): δ=154.8, 135.8, 116.7, 79.5, 74.7, 74.0, 52.7, 52.4, 49.0, 48.7, 45.5, 45.0, 35.6 and 28.7 ppm; MS (ESI): 250 ([MNa]$^+$, 100%); HRMS (ESI): found: 250.1416, C$_{12}$H$_{21}$NO$_3$Na ([MNa]$^+$) requires: 250.1419.

Example 6.2: (±)-trans-4-Allyl-3-hydroxy-pyrrolidine (11, X=allyl)

Concentrated HCl (1 mL, 33 mmol) is added to a stirred solution of Boo-protected amine 10 (X=allyl) (59 mg, 0.26 mmol) in methanol (5 mL). The reaction mixture is concentrated under reduced pressure and subsequently azetroped with methanol (10 mL) then toluene (10 mL). The residue is absorbed onto silica and eluted down a flash column (5:4.5:0.5, DCM:MeOH:NH$_4$OH) to afford the title compound (11, X=allyl) as a yellow oil (40 mg, 95%). $^{13}$C NMR (125 MHz, CD$_3$OD): δ=136.7, 116.7, 77.4, 54.3, 51.0, 48.3 and 37.3 ppm; MS (ESI): 128 ([MH]$^+$, 100%); HRMS (ESI): found: 128.1072, C$_7$H$_{14}$NO ([MH]$^+$) requires: 128.1075.

Example 6.3: (±)-trans-4-Allyl-1-[(9-deaza-adenin-9-yl)methyl]-3-hydroxypyrrolidine (1, X=allyl, A=CH, B=NH$_2$, D=H)

Formaldehyde (44 μL, 0.54 mmol, 37 wt % solution in water) followed by 9-deazaadenine (44 mg, 0.33 mmol) are added to a solution of amine 11 (X=allyl) (40 mg, 0.32 mmol) in 1,4-dioxane (0.6 mL) and water (1.2 mL). The reaction mixture is stirred at room temperature for 17 h, absorbed on to silica and eluted down a silica column with a gradient of 5% to 400% (7 N NH$_3$ in MeOH) in CH$_2$Cl$_2$. The crude product is collected, concentrated and subject to flash chromatography (5:4.9:0.1, CH$_2$Cl$_2$:MeOH:NH$_4$OH) to afford the title compound 1 (X=allyl, A=CH, B=NH$_2$, D=H) as an off-white solid (20 mg, 24%). $^{13}$C NMR (125 MHz, CD$_3$OD): δ=152.0, 151.0, 147.0, 138.0, 130.1, 116.3, 115.1, 112.5, 76.8, 62.2, 59.0, 49.1, 48.0 and 38.2 ppm; MS (ESI): 274 ([MH]$^+$, 100%); HRMS (ESI): found: 274.1661, C$_{74}$H$_{20}$N$_5$O ([MH]$^+$) requires: 274.1668.

Example 7: (±)-3,4-trans-1-[(9-Deaza-adenin-9-yl)methyl]-4-ethynyl-3-hydroxypyrrolidine (1, X=ethynyl, A=CH, B=NH$_2$, D=H)

Example 7.1: tert-butyl (±)-trans-3-Hydroxy-4-((trimethylsilyl)ethynyl)pyrrolidine-1-carboxylate (10, X=trimethylsilylethynyl)

n-Butyllithium (4.6 mL, 6.0 mmol, 1.3 M solution in hexanes) is added, over 5 min, to a solution of trimethylsilylacetylene (1.1 mL, 7.8 mmol) in THF (8.5 mL) at −78° C. After 30 min BF$_3$.OEt$_2$ (1.4 mL, 11.4 mmol) is added over 5 min. After stirring for a further 30 min at −78° C. a solution of epoxide (10, X=trimethylsilylethynyl) (550 mg, 3.0 mmol) in THF (10 mL) is added. The reaction mixture is stirred at −78° C. for 1.5 h then allowed to warm to room temperature. The reaction is stirred for 16 h then quenched by the addition of saturated aqueous solution of NH$_4$Cl (20 mL), then partitioned between water (50 mL) and EtOAc (50 mL). The layers are separated and the aqueous phase is extracted into EtOAc (3×50 mL). The combined organic phase is washed with brine (2×50 mL), dried (MgSO$_4$), filtered and concentrated under reduced pressure. Flash chromatography of the residue (2:8, EtOAc:Petrol) affords the title compound as a yellow gum (478 mg, 57%). $^{13}$C NMR (125 MHz, CDCl$_3$): δ=154.7, 104.7, 87.8, 79.8, 75.5, 74.7, 52.4, 52.1, 39.2, 38.7, 28.5 and 0.0 ppm; MS (ESI): 306 ([MNa]$^+$, 100%); HRMS (ESI): found: 306.1505, C$_{14}$H$_{25}$NO$_3$NaSi ([MNa]$^+$) requires: 306.1501.

Example 7.2: (±)-trans-3-hydroxy-4-((trimethylsilyl)ethynyl)pyrrolidine (11, X=trimethylsilylethynyl)

Concentrated HCl (1 mL, 33 mmol) is added to a solution of Boc-protected amine (10, X=trimethylsilylethynyl) (478 mg, 1.7 mmol) in methanol (20 mL) and then concentrated under reduced pressure. The residue is azetroped with methanol (20 mL) and toluene (20 mL) then absorbed on to silica and eluted down a flash column (5:4.8:0.2, DCM MeOH:NH$_4$OH) to afford the title compound (11, X=trimethylsilylethynyl) as a yellow solid (276 mg, 89%). $^{13}$C NMR (125 MHz, CD$_3$OD): δ=107.6, 87.6, 79.0, 54.8, 52.8, 41.8 and 0.0 ppm; MS (ESI): 184 ([MH]$^+$, 100%); HRMS (ESI): found: 184.1161, C$_8$H$_{18}$NOSi ([MH]$^+$) requires: 184.1158.

Example 7.3: (±)-trans-1-[(9-Deaza-adenin-9-yl)methyl]-3-hydroxy-4-((trimethylsilyl)ethynyl)pyrrolidine (1, X=trimethylsilylethynyl, A=CH, B=NH$_2$, D=H)

Formaldehyde (55 μL, 0.69 mmol, 37 wt % solution in water) followed by 9-deazaadenine (73 mg, 0.54 mmol) are added to a solution of amine 11 (X=trimethylsilylethynyl) (81 mg, 0.44 mmol) in 1,4-dioxane (2.5 mL) and water (2.5 mL). The reaction mixture is stirred at room temperature for 66 h, then concentrated under reduced pressure. The crude product containing title compound 1 (X=trimethylsilylethynyl, A=CH, B=NH$_2$, D=H) is used directly in the next step.

Example 7.4: (±)-trans-1-[(9-Deaza-adenin-9-yl)methyl]-4-ethynyl-3-hydroxypyrrolidine (1, X=ethynyl, A=CH, B=NH$_2$, D=H)

Sodium methoxide (10 μL, 0.05 mmol, 30 wt % solution in methanol) is added to a solution of the crude product above containing TMS-protected acetylene 1 (X=trimethylsilylethynyl, A=CH, B=NH$_2$, D=H) (145 mg, 0.44 mmol) in methanol (5 mL). The reaction mixture is stirred at room temperature for 2.5 h then further sodium methoxide (10 µL, 0.05 mmol, 30 wt % solution in methanol) is added. After stirring for a further 17 h the reaction mixture is absorbed onto silica and eluted down a silica column (5:4.95:0.05, CH$_2$Cl$_2$:MeOH:NH$_4$OH) to afford the crude product. Further purification by Prep HPLC affords the title compound 1 (X=ethynyl, A=CH, B=NH$_2$, D=H) as a pale yellow solid, (29 mg, 26%). $^{13}$C NMR (125 MHz, CD$_3$OD): δ=152.2, 151.0, 146.3, 130.5, 115.2, 111.1, 84.5, 78.0, 72.1, 61.5, 59.2, 49.1 and 39.8 ppm.

Example 8: (±)-trans-1-[(9-Deaza-adenin-9-yl)methyl]-4-butyl-3-hydroxypyrrolidine, it X=butyl, A=CH, B=NH$_2$, D=H)

Example 8.1: Benzyl (±)-trans-4-butyl-3-hydroxy-pyrrolidine-1-carboxylate (6, X=butyl)

A solution of epoxide 5 (80 mg, 0.4 mmol) and CuBr.SMe$_2$ (7 mg, 0.03 mmol) in THF (3 mL) is cooled to −30° C. n-Butylmagnesium chloride (1 mL, 2 mmol, 2 M solution in THF) is added drop-wise over 10 min, keeping the temperature below −25° C. After complete addition the reaction is allowed to warm to −15° C. over 45 min then quenched with 10% aqueous solution NH$_4$Cl (10 mL) and EtOAc (20 mL). The mixture is stirred at room temperature for 1 h 15 min then the layers are separated. The aqueous phase is extracted into EtOAc (2×20 mL). The combined organic phase is dried (MgSO$_4$), filtered and concentrated under reduced pressure. Flash chromatography of the residue (4:6 then 1:1, EtOAc:Petrol) affords the title compound 6 (X=butyl) as a pale yellow oil (72 mg, 71%).

Example 8.2: (±)-trans-4-Butyl-3-hydroxypyrrolidine (11, X=butyl)

Palladium (10 mg, 0.01 mmol, 10 wt % on carbon) is added to a solution of Cbz-protected amine 6 (X=butyl) (70 mg, 0.3 mmol) in MeOH (4 mL) under Argon. The reaction mixture is placed under a hydrogen atmosphere and stirred for 1.5 h, then filtered through Celite and concentrated under reduced pressure. Flash chromatography of the residue (5:4.8:0.2 then 5:4:5:0.5, CH$_2$Cl$_2$:MeOH:NH$_4$OH) affords the title compound 11 (X=butyl) as a yellow oil (20 mg, 54%). $^{13}$C NMR (125 MHz, CD$_3$OD): δ=75.3, 52.4, 50.0, 47.3, 31.9, 31.0, 23.6 and 14.3 ppm; MS (ESI): 144 ([MH]$^+$, 100%); HRMS (ESI): found: 144.1390, C$_8$H$_{16}$NO ([MH]$^+$) requires: 144.1388.

Example 8.3: (±)-trans-4-Butyl-1-[(9-deaza-adenin-9-yl)methyl]-3-hydroxypyrrolidine (1, X=butyl, A=CH, B=NH$_2$, D=H)

Formaldehyde (95 µL, 1.2 mmol, 37 wt % solution in water) followed by 9-deazaadenine (100 mg, 0.7 mmol) are added to a solution of amine 11 (X=butyl) (88 mg, 0.66 mmol) in 1,4-dioxane (1.2 mL) and water (2.5 mL). The reaction mixture is stirred at room temperature for 66 h, absorbed on to silica and eluted down a silica column using a gradient 10-20% (7 N NH$_3$ in MeOH) in CH$_2$Cl$_2$. The crude product is collected, concentrated and subject to flash chromatography (5:4.8:0.2, CH$_2$Cl$_2$:MeOH:NH$_4$OH) to afford the title compound 1 (X=butyl, A=CH, B=NH$_2$, D=H) as a pale yellow solid (89 mg, 47%). $^{13}$C NMR (125 MHz, CD$_3$OD): δ=152.1, 151.0, 147.0, 130.1, 115.2, 112.4, 77.7, 62.3, 59.69, 49.0, 48.5, 34.0, 31.5, 23.8 and 14.3 ppm; MS (ESI): 290 ([MH]$^+$, 100%); HRMS (ESI): found: 290.1989, C$_{15}$H$_{24}$N$_5$O ([MH]$^+$) requires: 290.1981.

Example 9: (±)-trans-1-[(9-Deaza-adenin-9-yl)methyl]-3-hydroxy-4-isobutylpyrrolidine (1, X=isobutyl, A=CH, B=NH$_2$, D=H)

Example 9.1: Benzyl (±)-trans-3-hydroxy-4-isobutylpyrrolidine-1-carboxylate

A solution of epoxide 6 (203 mg, 0.93 mmol) and CuBr.SMe$_2$ (30 mg, 0.15 mmol) in THF (8 mL) is cooled to −30° C. iso-Butylmagnesium bromide (2.3 mL, 4.6 mmol, 2 M solution in THF) is added drop-wise over 10 min, keeping the temperature below −27° C. After complete addition the reaction is allowed to warm to −15° C. over 1 h 20 min then quenched with 10% aqueous solution NH$_4$Cl (20 mL) and EtOAc (50 mL). The mixture is stirred at room temperature for 45 min then the layers are separated. The aqueous phase is extracted into EtOAc (2×50 mL). The combined organic phase is dried (MgSO$_4$), filtered and concentrated under reduced pressure to afford the crude product (193 mg, 75%) containing title compound 6 (X=isobutyl). This material is used in the next step without further purification.

Example 9.2: (±)-trans-3-Hydroxy-4-isobutylpyrrolidine

Palladium (20 mg, 0.02 mmol, 10 wt % on carbon) is added to a solution of the above crude product containing Cbz-protected amine 6 (X=isobutyl) (190 mg, 0.7 mmol) in MeOH (10 mL) under Argon. The reaction mixture is placed under a hydrogen atmosphere and stirred for 2 h, then filtered through Celite and concentrated under reduced pressure. Flash chromatography of the residue (gradient 5:4.8: 0.2 to 5:4:1, CH$_2$Cl$_2$:MeOH:NH$_4$OH) affords the title compound as a yellow oil (50 mg, 49%). $^{13}$C NMR (125 MHz, CD$_3$OD): δ=75.6, 52.5, 50.2, 45.3, 41.4, 27.4, 23.2 and 22.6 ppm; MS (ESI): 144 ([MH]$^+$, 100%); HRMS (ESI): found: 144.1382, C$_8$H$_{18}$NO ([MH]$^+$) requires: 144.1388.

Example 9.3: (±)-3,4-trans-1-[(9-Deaza-adenin-9-yl)methyl]-3-hydroxy-4-isobutylpyrrolidine (1, X=Isobutyl, A=CH, B=NH$_2$, D=H)

Formaldehyde (75 µL, 0.9 mmol, 37 wt % solution in water) followed by 9-deazaadenine (52 mg, 0.4 mmol) are added to a solution of amine 11 (X=isobutyl) (49 mg, 0.34 mmol) in 1,4-dioxane (0.6 mL) and water (1.2 mL). The reaction mixture is stirred at room temperature for 17 h, absorbed on to silica and eluted down a silica column with 10% (7 N NH$_3$ in MeOH) in CH$_2$Cl$_2$. The crude product is collected, concentrated and subject to flash chromatography (5:4.9:0.1, CH$_2$Cl$_2$:MeOH:NH$_4$OH) to afford the title compound 1 (X=isobutyl, A=CH, B=NH$_2$, D=H) as an off-white solid (42 mg, 42%). $^{13}$C NMR (125 MHz, CD$_3$OD): δ=152.1, 150.1, 147.0, 130.1, 115.1, 112.6, 78.1, 62.3, 59.8, 49.1, 46.2, 43.9, 27.7, 23.6 and 22.7 ppm; MS (ESI): 312 ([MNa]$^+$, 35%), 290 ([MH]$^+$, 100%); HRMS (ESI): found: 290.1979, C$_{15}$H$_{24}$N$_5$O ([MH]$^+$) requires: 290.1981.

Example 10: (±)-trans-1-[(9-Deaza-adenin-9-yl) methyl]-3-hydroxy-4-(pent-3-yl)pyrrolidine (1, X=pent-3-yl, A=CH, B=NH$_2$, D=H)

Example 10.1: Benzyl (±)-trans-3-hydroxy-4-(pent-3-yl)pyrrolidine-1-carboxylate (6, X=pent-3-yl)

A solution of epoxide 5 (230 mg, 1.05 mmol) and CuBr.DMS (28 mg, 0.22 mmol) in THF (10 mL) is cooled to −30° C. 3-Pentylmagnesium bromide (2.3 mL, 4.6 mmol, 2 M solution in ether) is added drop-wise over 10 min. After complete addition the reaction is allowed to warm to −20° C. over 30 min then quenched with 10% aqueous solution NH$_4$Cl (40 mL) and EtOAc (40 mL). The mixture is stirred at room temperature for 1 h then the layers are separated. The aqueous phase is extracted into EtOAc (3×40 mL). The combined organic phase is dried (MgSO$_4$), filtered and concentrated under reduced pressure. Flash chromatography of the residue (2:8, EtOAc: Petrol) affords the title compound 6 (X=pent-3-yl) and an unknown co-running impurity as a pale yellow oil (195 mg).

Example 10.2: (±)-trans-3-Hydroxy-4-(pent-3-yl) pyrrolidine (11, X=pent-3-yl)

Palladium (35 mg, 0.03 mmol, 10 wt % on carbon) is added to a solution of Cbz-protected amine 6 (X=pent-3-yl) (195 mg, 0.9 mmol) in MeOH (10 mL) under Argon. The reaction mixture is placed under a hydrogen atmosphere and stirred for 1 h, then filtered through Celite and concentrated under reduced pressure. Flash chromatography of the residue (5:4.9:0.1 then 5:4.8:0.2, CH$_2$Cl$_2$:MeOH:NH$_4$OH) affords the title compound 11 (X=pent-3-yl) as a pale yellow gum (27 mg, 16% over 2 steps). $^{13}$C NMR (125 MHz, CD$_3$OD): δ=76.7, 56.0, 52.1, 50.5, 43.4, 24.4, 23.6, 11.4 and 11.0 ppm; MS (ESI): 158 ([MH]$^+$, 100%); HRMS (ESI): found: 158.1540, C$_9$H$_{20}$NO ([MH]$^+$) an requires: 158.1545.

Example 10.3: (±)-trans-1-[(9-Deaza-adenin-9-yl) methyl]-3-hydroxy-4-(pent-3-yl)pyrrolidine (1, X=pent-3-yl, A=CH, B=NH$_2$, D=H)

Formaldehyde (25 μL, 0.3 mmol, 37 wt % solution in water) followed by 9-deazaadenine (30 mg, 0.22 mmol) are added to a solution of amine 11 (X=pent-3-yl) (27 mg, 0.17 mmol) in 1,4-dioxane (0.6 mL) and water (0.6 mL). The reaction mixture is stirred at room temperature for 17 h, absorbed on to silica and eluted down a silica column with a gradient of 5% to 20% (7 N NH$_3$ in MeOH) in CH$_2$Cl$_2$. The crude product is collected, concentrated and subject to flash chromatography (5:4.9:0.1, CH$_2$Cl$_2$:MeOH NH$_4$OH) to afford the title compound 1 (X=pent-3-yl, A=CH, B=NH$_2$, D=H) as a pale yellow solid (24 mg, 33%). $^{13}$C NMR (125 MHz, CD$_3$OD): δ=152.1, 151.0, 147.0, 130.1, 115.2, 112.5, 75.8, 63.3, 58.2, 51.3, 49.1, 44.3, 24.0, 23.6, 11.3 and 10.7 ppm; MS (ESI): 304 ([MH]$^+$, 100%); HRMS (ESI): found: 304.2137, C$_{16}$H$_{26}$N$_5$O ([MH]$^+$) requires: 304.2137

Example 11: (±)-trans-1-[(9-Deaza-adenin-9-yl) methyl]-4-ethyl-3-hydroxypyrrolidine (1, X=Ethyl, A=CH, B=D=H)

Example 11.1: Benzyl (±)-trans-4-ethyl-3-hydroxy-pyrrolidine-1-carboxylate

A solution of epoxide 5 (467 mg, 2.13 mmol) and CuBr.DMS (53 mg, 0.26 mmol) in THF (20 mL) is cooled to −30° C. Ethylmagnesium bromide (10 mL, 10 mmol, 1 M solution in THF) is added drop-wise over 20 min, keeping the temperature below −30° C. After complete addition the reaction is allowed to warm to −15° C. over 50 min then quenched with 10% aqueous solution NH$_4$Cl (20 mL) and EtOAc (40 mL). The mixture is stirred at room temperature for 45 min then the layers are separated. The aqueous phase is extracted into EtOAc (3×50 mL). The combined organic phase is dried (MgSO$_4$), filtered and concentrated under reduced pressure. Flash chromatography of the residue (3:7 then 4:6, EtOAc:Petrol) affords the title compound 6 (X=ethyl) as a pale yellow oil (370 mg, 70%).

Example 11.2: (±)-trans-4-Ethyl-3-hydroxypyrrolidine (11, X=ethyl)

Palladium (20 mg, 0.02 mmol, 10 wt % on carbon) is added to a solution of Cbz-protected amine 6 (X=ethyl) (270 mg, 1.1 mmol) in MeOH (10 mL) under Argon. The reaction mixture is placed under a hydrogen atmosphere and stirred for 1 h, then filtered through Celite and concentrated under reduced pressure. Flash chromatography of the residue (5:4: 1, CH$_2$Cl$_2$:MeOH:NH$_4$OH) affords the title compound 11 (X=ethyl) as a yellow oil (70 mg, 56%). $^{13}$C NMR (125 MHz, CD$_3$OD): δ=78.1, 54.7, 51.6, 51.0, 26.3 and 12.9 ppm; MS (ESI): 116 ([MH]$^+$, 100%).; HRMS (ESI): found: 116.1070, C$_6$H$_{14}$NO ([MH]$^+$) requires: 116.1075

Example 11.3: (±)-trans-1-[(9-Deaza-adenin-9-yl) methyl]-4-ethyl-3-hydroxypyrrolidine (1, X=ethyl, A=CH, B=NH$_2$, D=H)

Formaldehyde (120 μL, 1.5 mmol, 37 wt % solution in water) followed by 9-deazaadenine (102 mg, 0.9 mmol) are added to a solution of amine 11 (X=ethyl) (116 mg, 0.87 mmol) in 1,4-dioxane (1.6 mL) and water (3.2 mL). The reaction mixture is stirred at room temperature for 15 h, absorbed on to silica and eluted down a silica column using a gradient 5-30% (7 N NH$_3$ in MeOH) in CH$_2$Cl$_2$. The crude product is collected, concentrated and subject to flash chromatography (5:4.9:0.1 then 5:4.8:0.2, CH$_2$Cl$_2$:MeOH: NH$_4$OH) to afford the title compound 1 (X=ethyl, A=CH, B=NH$_2$, D=H) as a pale yellow solid (175 mg, 77%). $^{13}$C NMR (125 MHz, CD$_3$OD): δ=152.1, 151.0, 147.0, 130.1, 115.1, 112.5, 77.4, 62.4, 59.4, 50.4, 49.1, 27.1 and 12.9 ppm; MS (ESI): 262 ([MH$^+$, 100%); HRMS (ESI): found: 262.1664, C$_{13}$H$_{20}$N$_5$O ([MH]$^+$) requires: 262.1668.

Example 12: (3R,4S)-1-[9-Deaza-adenin-9-yl) methyl]-4-ethyl-3-hydroxypyrrolidine (20, R=H)

Example 12.1: (3R,4R)-tert-butyl 4-(benzoyloxymethyl)-3-hydroxypyrrolidine-1-carboxylate (13)

A solution of alcohol 12 (4.10 g, 19 mmol) and dibutyltin oxide (5.17 g, 21 mmol) in toluene (60 mL) is refluxed in a Dean-Stark apparatus for 1 h. The solution is cooled to 5° C. and benzoyl chloride (2.2 mL, 19 mmol) is added drop wise while the temperature is kept below 10° C. The mixture is stirred at room temperature for 17 h then concentrated under reduced pressure. Flash chromatography of the residue (40% EtOAc in Petrol) affords the title compound 13 as a yellow oil (2.48 g, 41%). $^{13}$C-NMR (125 MHz, CDCl$_3$): δ=171.3, 166.6, 154.6, 133.2, 129.6, 128.5, 79.7, 72.1, 71.4, 64.1, 60.4, 52.7, 52.5, 46.9, 46.4, 45.7, 45.2 and 28.5 ppm.

Example 12.2: (3R,4R)-tert-butyl 4-(benzoyloxymethyl)-3-(tert-butyldimethylsilyloxy)pyrrolidine-1-carboxylate (14)

tert-Butyldimethylsilyl chloride (2.33 g, 15 mmol) is added to a stirred solution of alcohol 13 (2.48 g, 7.7 mmol), imidazole (2.1 g, 31 mmol) in DMF (4 mL). The reaction mixture is stirred at room temperature for 17 h and diluted with toluene (50 mL) and water (50 mL). The phases are separated and the aqueous phase is extracted into toluene (2×50 mL). The combined organic phase is washed with water (2×50 mL) and brine (2×50 mL), dried ($MgSO_4$), filtered and concentrated under reduced pressure to afford the title compound 14 as a yellow oil (3.31 g, 98%). No further purification is required. $^1$H-NMR (500 MHz, $CDCl_3$): δ=8.02-7.99 (2H, br. m), 7.58-7.54 (1H, br. m), 7.46-7.41 (2H, br. m), 4.36-4.32 (1H, br. m), 4.27-4.18 (2H, br. m), 3.72-3.55 (2H, br. m), 3.32-3.15 (2H, br. m), 2.54-2.47 (1H, br. m), 1.45 (9H, d, J=4.6 Hz), 0.85 (9H, s) and 0.05 ppm (6H, br. s).

Example 12.3: (3R,4R)-tert-butyl 3-(tert-butyldimethylsilyloxy)-4-(hydroxymethyl)pyrrolidine-1-carboxylate (15)

Sodium methoxide (1.8 mL, 7.9 mmol, 25 wt % in methanol) is added to a solution of benzoyl ester 14 (3.31 g, 7.6 mmol) in methanol (10 mL). The reaction mixture is stirred at room temperature and after 3 h is diluted with chloroform (40 mL). The mixture is washed with water (2×20 mL), dried ($MgSO_4$), filtered and concentrated under reduced pressure. Flash chromatography of the residue (60% EtOAc in Petrol) affords the title compound 15 as a yellow oil (1.2 g, 47%). $^{13}$C-NMR (125 MHz, $CDCl_3$): δ=154.6, 79.4, 72.8, 72.1, 62.5, 62.4, 53.2, 52.5, 48.9, 48.3, 46.4, 45.9, 28.5, 25.8, 17.9 and −0.04 ppm.

Example 12.4: (3R,4S)-tert-butyl 3-(tert-butyldimethylsilyloxy)-4-formylpyrrolidine-1-carboxylate (16)

Alcohol 15 (1.1 g, 3.3 mmol) is added to a suspension of Dess-Martin periodinane (1.54 g, 3.6 mmol) in $CH_2Cl_2$ (30 mL). The reaction mixture is stirred at room temperature for 2.5 h and then diluted with ether (150 mL). The reaction mixture is washed with 1:1 solution of saturated sodium hydrogen carbonate:10% aqueous sodium thiosulfate (2×100 mL). The organic phase is dried ($MgSO_4$), filtered and concentrated under reduced pressure. Flash chromatography of the residue (1:9 then 2:8, EtOAc: Petrol) affords the title compound 16 as a pale yellow oil (980 mg, 90%). $^1$H NMR (500 MHz, $CDCl_3$): δ=9.67 (s, 1H), 4.54-4.52 (m, 1H), 3.68-3.53 (m, 3H), 3.19 (br. s, 1H), 2.96 (br. s, 1H), 1.43 (s, 9H), 0.86 (s, 9H) and 0.06 ppm (s, 6H). $^{13}$C NMR (125 MHz, $CDCl_3$): δ=199.7, 154.2, 79.8, 71.5, 70.9 (rotamers); 59.1, 58.4 (rotamers), 53.6, 53.0 (rotamers), 43.5, 28.4, 25.6, 17.9, −4.8 and −4.9 ppm.

Example 12.5: (3R,4S)-tert-butyl 3-(tert-butyldimethylsilyloxy)-4-vinylpyrrolidine-1-carboxylate (17)

n-Butyllithium (4.3 mL, 6.8 mmol, 1.6 M solution in hexanes) is added added drop-wise to a stirred suspension of methyltriphenylphosphonium bromide (2.44 g, 6.8 mmol) in THF (10 mL) at 0° C. After 30 min is added drop-wise to a solution of aldehyde 16 (977 mg, 3.0 mmol) in THF (10 mL) cooled to −78° C. After stirring at −78° C. for 1 h the reaction mixture is allowed to warm to room temperature for 2.5 h then quenched with water (30 mL) and extracted into $CH_2Cl_2$ (100 mL). The combined organic phase is washed with saturated aqueous sodium hydrogen carbonate (50 mL) and brine (50 mL), then dried ($MgSO_4$), filtered and concentrated under reduced pressure. Flash chromatography of the residue (1:9, EtOAc:Petrol) affords the title compound 17 as a colourless oil (867 mg, 89%). $^{13}$C-NMR (125 MHz, $CDCl_3$): δ=154.5, 136.6, 116.8, 79.3, 75.8, 74.8, 52.8, 52.3, 50.8, 50.0, 48.5, 48.0, 28.5, 25.7, 18.0 and −4.8 ppm; MS (ESI): 350 ([MNa]$^+$, 100%); HRMS (ESI): found: 350.2128, $C_{17}H_{33}NO_3SiNa$ ([MNa]$^+$) requires: 350.2127.

Example 12.6: (3R,4S)-tert-butyl 3-(tert-butyldimethylsilyloxy)-4-ethylpyrrolidine-1-carboxylate (18)

Palladium (100 mg, 0.9 mmol, 10 wt % on carbon) is added to a solution of olefin 17 (870 mg, 2.7 mmol) in ethanol (25 mL) under an Argon atmosphere. The reaction mixture is placed under a hydrogen atmosphere and stirred for 15 h, then filtered through Celite and concentrated under reduced pressure to afford the crude product 18 (770 mg, 88%). No further purification was necessary. $^{13}$C-NMR (125 MHz, $CDCl_3$): δ=154.7, 79.1, 75.5, 74.8, 53.4, 52.6, 49.0, 48.5, 48.3, 47.6, 29.3, 25.7, 24.3, 18.0, 14.0 and −0.04 ppm.

Example 12.7: (3R,4S)-4-Ethyl-3-hydroxypyrrolidine (19)

A solution of Boc-protected amine 18 (772 mg, 2.3 mmol) in TFA (20 mL, 260 mmol) is stirred at room temperature for 17 h, then concentrated under reduced pressure. The residue is dissolved in water (50 mL) and washed with chloroform (2×50 mL). The aqueous phase is absorbed onto silica and eluted down a silica column (5:4.5:0.5, DCM:MeOH:$NH_4OH$) to afford the title compound 19 as a yellow oil (205 mg, 76%). $^{13}$C NMR (125 MHz, $CD_3OD$): δ=78.1, 54.8, 51.6, 51.0, 26.3 and 13.0 ppm; MS (ESI): 116 ([MH]$^+$, 100%); [a]$_D^{21}$=+5.04 (c=1.15, MeOH).

Example 12.8: (3R,4S)-14[(9-Deaza-adenin-9-yl)methyl]-4-ethyl-3-hydroxypyrrolidine (20, R=H)

Formaldehyde (53 μL, 0.7 mmol, 37 wt % solution in water) followed by 9-deazaadenine (54 mg, 0.4 mmol) are added to a solution of (3R,4S)-4-ethyl-3-hydroxypyrrolidine (19) (44 mg, 0.38 mmol) in 1,4-dioxane (0.7 mL) and water (1.4 mL). The reaction mixture is stirred at room temperature for 66 h, absorbed on to silica and eluted down a silica column using a gradient 5-30% (7 N $NH_3$ in MeOH) in $CH_2Cl_2$. The crude product is collected, concentrated and subject to flash chromatography (5:4.9:0.1 then 5:4.8:0.2, $CH_2Cl_2$:MeOH:$NH_4OH$) to afford the title compound 20 (R=H) as an off-white solid (67 mg, 67%). $^{13}$C NMR (125 MHz, $CD_3OD$): δ=152.1, 151.0, 147.0, 130.1, 115.1, 112.6, 77.4, 62.4, 59.4, 50.4, 49.15, 27.1 and 12.9 ppm; MS (ESI): 262 ([MH$^+$, 100%); HRMS (ESI): found: 262.1665, $C_{13}H_{20}N_5O$ ([MH]$^+$) requires: 262.1668; [a]$_D^{21}$=+3.48 (c=1.03, MeOH).

Example 13: (±1-trans-4-Cyclopentyl-1-[9-deaza-adenin-9-yl)methyl]-3-hydroxypyrrolidine (1, X=cyclopentyl, A=CH, B=$NH_2$, D=H)

Example 13.1: Benzyl(±)-trans-4-cyclopentyl-3-hydroxypyrrolidine-1-carboxylate (6, X=cyclopentyl)

Cyclopentyl bromide (0.5 mL, 4.7 mmol) is added drop-wise to a suspension of magnesium (221 mg, 9 mmol) in THF (10 mL), activated with 1,2-dibromoethane. After complete addition the reaction mixture is stirred for 1 h at room temperature and then added drop-wise, over 10 min, to a solution of epoxide 8 (230 mg, 1 mmol) and CuBr-DMS (55 mg, 0.3 mmol) in THF (10 mL) at −30° C. (internal temperature). The reaction mixture is stirred for 75 min and then quenched with 10% aqueous NH$_4$Cl solution (20 mL) and EtOAc (20 mL). The bi-phasic mixture is stirred for 1 h and then the layers are separated, and the aqueous phase extracted with EtOAc (2×50 mL). The combined organic phases are dried (MgSO$_4$), filtered and concentrated under reduced pressure to afford the crude 6 (X=cyclopentyl) as a pale yellow oil, which is used immediately in the next step without characterisation.

Example 13.2: (±)-trans-4-cyclopentyl-3-hydroxypyrrolidine (11, X=cyclopentyl)

Palladium (50 mg, 0.05 mmol, 10 wt % on carbon) was added to a solution of crude 6, X=cyclopentyl in MeOH (20 mL) under argon. The reaction mixture is placed under a hydrogen atmosphere and stirred for 1 h and then further catalyst (50 mg) is added. The reaction mixture is placed under a hydrogen atmosphere for a further 1 h and then filtered through Celite® and concentrated under reduced pressure. Flash chromatography of the residue (5:4.6:0.4, CH$_2$Cl$_2$:MeOH: 28% aq. NH$_4$OH) affords crude 11 (X=cyclopentyl) (43 mg) which is used without further purification and characterisation in the next step.

Example 13.3: (±)-trans-4-Cyclopentyl-1-[(9-deazaadenin-9-yl)methyl]-3-hydroxypyrrolidine (1, X=cyclopentyl, A=CH, B=NH$_2$, D=H)

Formaldehyde (35 μL, 0.4 mmol, 37 wt % solution in water) followed by 9-deazaadenine (42 mg, 0.3 mmol) are added to a solution of crude 11 (X=cyclopentyl) (43 mg) in 1,4-dioxane (1 mL) and water (1 mL). The reaction mixture is stirred at room temperature for 94 h, absorbed onto silica and eluted down a silica column with a gradient of 5% to 30% (7 N NH$_3$ in MeOH) in CH$_2$Cl$_2$. The crude product is collected, concentrated and subjected to flash chromatography (5:4.95:0.05, CH$_2$Cl$_2$:MeOH:28% aq. NH$_4$OH) to afford title compound 1 (X=cyclopentyl, A=CH, B=NH$_2$, D=H) as an off-white solid (28 mg, 10%, over 3 steps). $^1$H NMR (500 MHz, CD$_3$OD): δ=8.16 (s, 1H), 7.50 (s, 1H), 3.97-3.94 (m, 1H), 3.85 (d, J=13.4 Hz, 1H), 3.80 (d, J=13.4 Hz, 1H), 3.06 (dd, J=9.6, 8.1 Hz, 1H), 2.76-2.68 (m, 2H), 2.39 (dd, J=9.7, 8.1 Hz, 1H), 1.89-1.50 (m, 8H), 1.34-1.30 (m, 1H) and 1.21-1.08 ppm (m, 1H). $^{13}$C NMR (125 MHz, CD$_3$OD): δ=152.1, 151.0, 147.0, 130.2, 115.2, 112.4, 76.7, 63.0, 59.1, 54.2, 49.1, 44.7, 32.2, 31.8 and 26.1 (2C) ppm. ESI-HRMS for C$_{16}$H$_{23}$N$_5$ONa [MNa]$^+$ calcd, 324.1800; found, 324.1802.

Example 14: (±)-trans-4-(1-Benzyl-1H-1,2,3-triazol-4-yl)-1-[(9-deaza-adenin-9-methyl]-3-hydroxypyrrolidine (1, X=1-Benzyl-1H-1,2,3- triazol-4-yl, A=CH, B=NH$_2$, D=H)

Example 14.1: tert-Butyl (±)-trans-4-ethynyl-3-hydroxypyrrolidine-1-carboxylate (22)

Tetrabutylammonium fluoride (3 mL, 3 mmol, 1.0 M solution in THF) is added drop-wise to a stirred solution of 21 (for preparation, see Example 7.1, compound 10, X=trimethylsilylethynyl) (569 mg, 2 mmol) in THF (15 mL). After stirring for 1 h at room temperature the reaction mixture is quenched by the addition of water (100 mL) and then extracted with EtOAc (3×75 mL). The combined organic phase is washed with brine (80 mL) and then dried (MgSO$_4$), filtered and concentrated under reduced pressure to afford crude 22 as a yellow oil (420 mg, 99%). No further purification is necessary. $^1$H NMR (500 MHz, CDCl$_3$): δ=4.26 (dd, J=8.4, 3.8 Hz, 1H), 3.63-3.56 (m, 2H), 3.39-3.32 (m, 1H), 3.22 (t, J=11.5 Hz, 1H), 2.83 (br. s, 1H), 2.11 (br. s, 1H) and 1.37 ppm (s, 9H). $^{13}$C NMR (125 MHz, CDCl$_3$): δ=154.7, 82.7, 79.9, 75.0, 74.2 (rotamers), 71.3, 52.3, 52.1 (rotamers), 49.7, 49.2 (rotamers), 37.8, 37.2 (rotamers) and 28.4 ppm. ESI-HRMS for C$_{11}$H$_{17}$NO$_3$$^{23}$Na [MNa]$^+$ calcd, 234.1106; found, 234.1108.

Example 14.2: tert-Butyl (±)-trans-4-(1-benzyl-1H-1,2,3-triazol-4-yl)-3-hydroxypyrrolidine-1-carboxylate (23)

Sodium ascorbate (14 mg, 0.07 mmol) and then copper(II) sulphate (20 μL, 0.02 mmol, 1.0 M aqueous solution) are added to a solution of 22 (122 mg, 0.6 mmol) and benzyl azide (111 mg, 0.8 mmol) in t-BuOH (1 mL) and water (1 mL). After stirring at room temperature for 18.5 h the mixture is partitioned between water (10 mL) and EtOAc (10 mL). The layers are separated and the aqueous phase was extracted with EtOAc (2×20 mL). The combined organic phases are washed with 5% aqueous NH$_4$OH solution (2×20 mL) and brine (20 mL), dried (MgSO$_4$), filtered and concentrated under reduced pressure. Flash chromatography of the residue (gradient 50-100% EtOAc in Petrol) affords 23 as a yellow oil (114 mg, 57%). $^1$H NMR (500 MHz, CDCl$_3$): δ=7.34-7.30 (m, 4H), 7.22-7.21 (m, 2H), 5.44 (s, 2H), 4.43 (br. d, J=38 Hz, 1H), 4.18 (d, J=11.0 Hz, 1H), 3.83 (dd, J=11.0, 7.6 Hz, 1H), 3.67-3.58 (m, 1H), 3.51-3.44 (m, 1H), 3.41-3.33 (m, 1H), 3.29-3.25 (m, 1H) and 1.40 ppm (s, 9H). $^{13}$C NMR (125 MHz, CDCl$_3$): δ=154.6, 154.5 (rotamers), 147.2, 147.0 (rotamers), 134.5, 129.1, 128.8, 128.1, 120.9, 79.6, 74.9, 74.1 (rotamers), 54.2, 52.2, 51.9 (rotamers), 49.1, 48.6 (rotamers), 43.5, 43.0 (rotamers) and 28.5 ppm. ESI-HRMS for C$_{18}$H$_{24}$N$_4$O$_3$Na [MNa]$^+$ calcd, 367.1746; found, 367.1747.

Example 14.3: (±)-trans-4-(1-Benzyl-1H-1,2,3-triazol-4-yl)-3-hydroxypyrrolidine (24)

36% aq. HCl (500 μL, 16 mmol) is added to a solution of 23 (114 mg, 0.3 mmol) in methanol (10 mL). The reaction mixture is concentrated under reduced pressure and then azeotroped with methanol (2×20 mL) followed by toluene (10 mL). Flash chromatography of the residue (20% (7N NH$_3$ in MeOH) in CH$_2$Cl$_2$) affords 24 as an off-white solid (60 mg, 74%). $^1$H NMR (500 MHz, CD$_3$OD): δ=7.81 (s, 1H), 7.38-7.31 (m, 5H), 5.55 (s, 2H), 4.36 (dt, J=5.7, 3.9 Hz, 1H), 3.43 (dd, J=11.4, 7.8, 1H), 3.29-3.25 (m, 1H), 3.14 (dd, J=12.1, 5.7 Hz, 1H), 2.97 (dd, J=11.4, 6.5 Hz, 1H) and 2.85 ppm (dd, J=12.0, 3.7 Hz, 1H). $^{13}$C NMR (125 MHz, CD$_3$OD): δ=149.8, 136.8, 130.0, 129.6, 126.2, 123.1, 78.9, 55.1, 54.9, 52.4 and 46.8 ppm. ESI-HRMS for C$_{13}$H$_{17}$N$_4$O [MH]$^+$ calcd, 245.1402; found, 245.1401.

Example 14.4: (±)-trans-4-(1-Benzyl-1H-1,2,3-triazol-4-yl)-1-[(9-deaza-adenin-9-yl)methyl]-3-hydroxypyrrolidine (1, X=1-benzyl-1H-1,2,3-triazol-4-yl, A=CH, B=NH$_2$, D=H)

Formaldehyde (35 μL, 0.44 mmol, 37 wt % solution in water) followed by 9-deazaadenine (40 mg, 0.30 mmol) are added to a solution of 24 (60 mg, 0.25 mmol) in 1,4-dioxane (0.6 mL) and water (1.2 mL). The reaction mixture is stirred at room temperature for 17 h and then further formaldehyde (20 µL, 0.25 mmol, 37 wt % solution in water) is added. After stirring for 60 h the reaction mixture is absorbed onto silica and eluted down a silica column with a gradient of 10% to 30% (7 N NH$_3$ in MeOH) in CH$_2$Cl$_2$. The crude product is collected, concentrated and subjected to flash chromatography (5:4.9:0.1, CH$_2$Cl$_2$:MeOH: 28% aq. NH$_4$OH) to afford 1 (X=1-benzyl-1H-1,2,3-triazol-4-yl, A=CH, B=NH$_2$, D=H) as an off-white solid (49 mg, 51%). $^1$H NMR (500 MHz, CD$_3$OD): δ=8.14 (s, 1H), 7.79 (s, 1H), 7.48 (s, 1H), 7.37-7.29 (m, 5H), 5.53 (s, 2H), 4.33-4.30 (m, 1H), 3.89 (d, J=13.4 Hz, 1H), 3.84 (d, J=13.4 Hz, 1H), 3.25-3.21 (m, 1H), 2.96 (dd, J=10.3, 6.8 Hz, 1H), 2.77 (dd, J=10.3, 4.0 Hz, 1H) and 2.68-2.65 ppm (m, 1H). $^{13}$C NMR (125 MHz, CD$_3$OD): δ=152.1, 151.0, 150.3, 147.0, 136.8, 130.0 (2C), 129.6, 129.1, 123.1, 115.2, 112.7, 77.8, 62.2, 59.4, 54.9, 48.9 and 46.2 ppm. ESI-HRMS for C$_{20}$H$_{23}$N$_8$O [MH]$^+$ calcd, 391.1995; found, 391.1994.

Example 15: (±)-trans-1-[(9-Deaza-adenin-9-yl) methyl]-3-hydroxy-4-(1H-1,2,3-triazol-4-yl)pyrrolidine (1, X=1-H-1,2,3-triazol-1-H-1,2,3-triazol-1-yl, A=CH, B=NH$_2$, D=H)

Example 15.1: tert-Butyl (±)-trans-4-azido-3-hydroxypyrrolidine-1-carboxylate (25)

(Tsuzuki, Y.; Chiba, K.; Mizuno, K.; Tomita, K.; Suzuki, K. Practical Synthesis of (3S, 4S)-3-methoxy-4-methylpyrrolidine. *Tetrahedron: Asymmetry* 2002, 12, 2989-2997)

Sodium azide (1.02 g, 15.7 mmol) is added to a solution of epoxide 5 (Prot=CO$_2$Bu$^t$) (1.0 g, 5.4 mmol) in 1,4-dioxane (9 mL) and water (1.8 mL). The resulting suspension is heated to 100° C. for 65 h and then cooled to 0° C. and water (20 mL) is added. The mixture is extracted with EtOAc (3×50 mL) and the combined organic phases are washed with brine (50 mL), dried (MgSO$_4$), filtered and concentrated under reduced pressure. Flash chromatography of the residue (3:7, then 4:6, ETOAc:Petrol) affords 25 as a pale yellow oil (1.21 g, 98%). $^1$H NMR (500 MHz, CDCl$_3$): δ=4.23 (br. s, 1H), 3.93 (br. s, 1H), 3.70-3.66 (m, 1H), 3.60-3.56 (m, 1H), 3.46-3.16 (m, 3H) and 1.46 ppm (s, 9H). $^{13}$C NMR (125 MHz, CDCl$_3$): δ=154.6, 80.3, 74.1, 73.3 (rotamers), 65.4, 64.9 (rotamers), 51.9, 51.6 (rotamers), 48.7, 48.2 (rotamers) and 28.4 ppm. ESI-HRMS for C$_8$H$_{18}$N$_4$O$_3$Na [MNa]$^+$ calcd, 251.1120; found, 251.1121.

Example 15.2: tert-Butyl (±)-trans-3-hydroxy-4-(5-(trimethylsilyl)-1H-1,2,3-triazol-1-yl)pyrrolidine-1-carboxylate (26)

Trimethylsilylacetylene (2.2 mL, 15.6 mmol) is added to a solution of 25 (730 mg, 3.2 mmol) in toluene (35 mL). The resulting mixture is heated to reflux for 88 h and then allowed to cool and concentrated under reduced pressure to afford a mixture of 26 and 27. This mixture is used directly in the next step without characterisation.

Example 15.3: tert-Butyl (±)-trans-3-hydroxy-4-(1H-1,2,3-triazol-1-yl)pyrrolidine-1-carboxylate (27)

The mixture of 26 and 27 is taken up in THF (20 mL) and TBAF (4.8 mL, 4.8 mmol, 1 M solution in THF) is added. The reaction mixture is stirred for 4 h and then further TBAF (1.6 mL, 1.6 mmol, 1 M solution in THF) was added. The reaction mixture is stirred for a further 16 h and then partitioned between EtOAc (30 mL) and water (30 mL). The layers are separated and the aqueous phase is extracted with EtOAc (2×50 mL). The combined organic phases are washed with brine (2×50 mL), dried (MgSO$_4$), filtered and concentrated under reduced pressure. Flash chromatography of the residue (100% EtOAc) affords 27 as a pale yellow gum (510 mg, 63%, over 2 steps) and 26 is obtained as a pale yellow oil (140 mg, 14%). 27. $^1$H NMR (500 MHz, CDCl$_3$): δ=7.63 (d, J=6.8 Hz, 1H), 7.58 (s, 1H), 5.44 (br. s, 1H), 4.93-4.89 (m, 1H), 4.60 (d, J=15.9 Hz, 1H), 4.00 (dd, J=9.5, 7.2 Hz, 1H), 3.77-3.67 (m, 2H), 3.36 (dd, J=11.8, 4.6 Hz, 1H) and 1.38 ppm (s, 9H). $^{13}$C NMR (125 MHz, CDCl$_3$): δ=154.4, 154.2 (rotamers), 133.6, 123.1, 80.4, 74.2, 73.4 (rotamers), 65.4, 64.9 (rotamers), 51.7, 51.1 (rotamers), 48.8, 48.4 (rotamers) and 28.4 ppm. ESI-HRMS for C$_{11}$H$_{18}$N$_4$O$_3$Na [MNa]$^+$ calcd, 277.1277; found, 277.1275. 26. $^1$H NMR (500 MHz, CDCl$_3$): δ=7.51 (s, 1H), 4.92-4.78 (m, 2H), 4.49 (br. s, 1H), 4.10-4.03 (m, 1H), 3.89-3.79 (m, 2H), 3.44 (br. s, 1H), 1.47 (s, 9H) and 0.29 ppm (s, 9H). $^{13}$C NMR (125 MHz, CDCl$_3$): δ=155.6, 155.4 (rotamers), 147.7, 129.5, 81.5, 75.5, 74.6 (rotamers), 66.5, 66.0 (rotamers), 52.6, 52.1 (rotamers), 50.2, 49.7 (rotamers), 29.6 and 0.0 ppm. ESI-HRMS for C$_{14}$H$_{26}$N$_4$O$_3$NaSi [MNa]$^+$ calcd, 349.1672; found, 349.1669.

Example 15.4: (±)-trans-3-Hydroxy-4-(1H-1,2,3-triazol-1-yl)pyrrolidine 28

36% aq. HCl (1 mL, 33 mmol) is added to a solution of 27 (500 mg, 2.0 mmol) in methanol (25 mL). The reaction mixture is concentrated under reduced pressure and subsequently azeotroped with methanol (2×20 mL) followed by toluene (10 mL). Flash chromatography of the residue (5:4.6:0.4, CH$_2$Cl$_2$:MeOH:28% aq. NH$_4$OH) affords 28 as an off-white foam (185 mg, 61%). $^1$H NMR (500 MHz, CD$_3$OD): δ=8.06 (d, J=0.9 Hz, 1H), 7.75 (d, J=0.9 Hz, 1H), 4.94-4.91 (m, 1H), 4.54-4.51 (m, 1H), 3.58 (dd, J=12.5, 7.3 Hz, 1H), 3.37-3.34 (m, 1H), 3.27 (dd, J=12.6, 4.7 Hz, 1H) and 2.92 ppm (dd, J=12.2, 3.9 Hz, 1H). $^{13}$C NMR (125 MHz, CD$_3$OD): δ=134.5, 125.4, 78.7, 69.8, 54.7 and 52.3 ppm. ESI-HRMS for C$_6$H$_{11}$N$_4$O [MH]$^+$ calcd, 155.0933; found, 155.0931.

Example 15.5: (±)-trans-1-[(9-Deaza-adenin-9-yl) methyl]-3-hydroxy-4-(1H-1,2,3-triazol-1-yl)pyrrolidine (1, X=1H-1,2,3-triazol-1-yl, A=CH, B=NH$_2$, D=H)

Formaldehyde (75 µL, 0.9 mmol, 37 wt % solution in water) followed by 9-deazaadenine (100 mg, 0.75 mmol) are added to a solution of 28 (96 mg, 0.62 mmol) in 1,4-dioxane (1.5 mL) and water (1.5 mL). After stirring for 66 h the reaction mixture is absorbed onto silica and eluted down a silica column with a gradient of 10% to 20% (7 N NH$_3$ in MeOH) in CH$_2$Cl$_2$. The crude product is collected, concentrated and subjected to flash chromatography (5:4.98:0.02, CH$_2$Cl$_2$:MeOH: 28% aq. NH$_4$OH) to afford (1, X=1H-1,2,3-triazol-1-yl, A=CH, B=NH$_2$, D=H) (58 mg, 31%). A sample is purified by Prep HPLC to analytical purity as a TFA salt. $^1$H NMR (500 MHz, CD$_3$OD): δ=8.45 (s, 1H), 8.14 (d, J=0.8 Hz, 1H), 8.08 (s, 1H), 7.80 (d, J=0.7 Hz, 1H), 5.33 (dt, J=7.3, 2.8 Hz, 1H), 4.82 (s, 2H), 4.66 (p, J=2.2 Hz, 1H), 4.33 (dd, J=13.2, 7.5 Hz, 1H), 4.15 (dd, J=13.2, 3.6 Hz, 1H), 3.92 (m, J=12.4, 4.5 Hz, 1H) and 3.66 ppm (dd, J=12.3, 1.7 Hz, 1H). $^{13}$C NMR (125 MHz, CD$_3$OD): δ=152.0, 145.1, 139.9, 136.1, 135.1, 126.6, 114.1, 104.6, 75.8, 66.6, 60.3, 57.2 and 49.9 ppm (resonance signals due to CF$_3$COOH have not been quoted). ESI-HRMS for C$_{13}$H$_{17}$N$_8$O [MH]$^+$ calcd, 301.1525; found, 301.1530.

Example 16: (±)-trans-4-[3-(Benzythio)propyl]-1-[(9-deaza-adenin-9-yl)methyl]-3-hydroxypyrrolidine [1, X=3-(benzylthio)propyl, A=CH, B=NH$_2$, D=H]

Example 16.1: (±)-tert-Butyl trans-4-[(benzylthio) propyl]-3-hydroxypyrrolidine-1-carboxylate (29)

1,1'-Azobis(cyanocyclohexane) (20 mg, 0.08 mmol) is added to a solution of 10 (X=allyl) (245 mg, 1.1 mmol) and benzyl mercaptan (1.9 mL, 16 mmol) in 1,4-dioxane (1.9 mL). The reaction mixture is heated to 90° C. for 22 h, with further 1,1'-azobis(cyanocyclohexane) (32 mg, 0.1 mmol) being added at intervals of 3, 5 and 6 h. The reaction is allowed to cool and concentrated under reduced pressure. Flash chromatography of the residue (1:9 then 1:1, ETOAc: petrol) affords a 5:1 mixture of 29:10 (X=allyl) as a colourless oil (272 mg). $^1$H NMR (500 MHz, CDCl$_3$): δ=7.31-7.22 (m, 5H), 3.96 (br. s, 1H), 3.70 (s, 1H), 3.62-6.52 (m, 2H), 3.25-3.16 (m, 1H), 3.03-2.98 (m, 1H), 2.43-2.41 (m, 2H), 2.21-1.95 (m, 2H), 1.61-1.51 (m, 2H), 1.45 (s, 9H) and 1.30-1.24 ppm (m, 1H). $^{13}$C NMR (125 MHz, CDCl$_3$): δ=154.6, 138.5, 128.8, 128.5, 127.0, 79.4, 75.5, 74.7 (rotamers), 52.8, 52.5 (rotamers), 49.4, 48.9 (rotamers), 45.9, 45.4 (rotamers), 36.4, 35.7 (rotamers), 31.3, 30.6, 28.5 and 27.3 ppm. ESI-HRMS for C$_{19}$H$_{29}$NO$_3$NaS [MNa]$^+$ calcd, 374.1766; found, 374.1761.

Example 16.2: (±)-trans-4-[3-(Benzylthio)propyl]-3-hydroxypyrrolidine (30)

36% aq. HCl (500 µL, 16 mmol) is added to a solution of 29:10 (X=allyl) (272 mg, 5:1) in methanol (10 mL). The reaction mixture is concentrated under reduced pressure and then azeotroped with methanol (2×20 mL) followed by toluene (10 mL). Flash chromatography of the residue (5:4.6:0.4, CH$_2$Cl$_2$:MeOH: 28% aq. NH$_4$OH) affords 30 as a yellow oil (115 mg, 60% over 2 steps). $^1$H NMR (500 MHz, CD$_3$OD): δ=7.33-7.28 (m, 4H), 7.23-7.20 (m, 1H), 4.14 (s, 1H), 3.72 (s, 2H), 3.53-3.49 (m, 1H), 3.38-3.35 (m, 1H), 3.14 (d, J=12.3 Hz, 1H), 2.96 (dd, J=11.6, 5.5 Hz, 1H), 2.47-2.44 (m, 2H), 2.16 (br. s, 1H), 1.64-1.50 (m, 3H) and 1.39-1.32 ppm (m, 1H). $^{13}$C NMR (125 MHz, CD$_3$OD): δ=140.3, 130.0, 129.5, 128.0, 75.1, 52.5, 49.9, 47.0, 37.1, 32.1, 31.2 and 28.5 ppm. ESI-HRMS for C$_{14}$H$_{22}$NOS [MH]$^+$ calcd, 252.1422; found, 252.1417.

Example 16.3: (±)-trans-4-[3-(Benzylthio)propyl]-1-[(9-deaza-adenin-9-yl)methyl]-3-hydroxypyrrolidine [1, X=3-(benzylthio)propyl, A=CH, B=NH$_2$, D=H]

Formaldehyde (40 µL, 0.5 mmol, 37 wt % solution in water) followed by 9-deazaadenine (46 mg, 0.3 mmol) are added to a solution of 30 (75 mg, 0.3 mmol) in 1,4-dioxane (0.8 mL) and water (0.8 mL). After stirring for 16 h the reaction mixture is absorbed onto silica and eluted down a silica column with a gradient of 5% to 50% (7 N NH$_3$ in MeOH) in CH$_2$Cl$_2$. The crude product is collected, concentrated and subjected to flash chromatography (5:4.95:0.05 then 5:4.8:0.2, CH$_2$Cl$_2$:MeOH: 28% aq. NH$_4$OH) to afford 1 (X=3-(benzylthio)propyl, A=CH, B=NH$_2$, D=H) as an off-white solid (23 mg, 20%). $^1$H NMR (500 MHz, CD$_3$OD): δ=8.16 (s, 1H), 7.48 (s, 1H), 7.30-7.23 (m, 4H), 7.18-7.15 (m, 1H), 3.83-3.79 (m, 3H), 3.67 (s, 2H), 3.00 (t, J=8.3 Hz, 1H), 2.74 (dd, J=10.4, 6.4 Hz, 1H), 2.67 (dd, J=10.3, 4.0 Hz, 1H), 2.38 (t, J=7.0 Hz, 1H), 2.13 (dd, J=9.6, 8.0 Hz, 1H), 1.92-1.86 (m, 1H), 1.97-1.48 (m, 3H) and 1.37-1.30 ppm (m, 1H). $^{13}$C NMR (125 MHz, CD$_3$OD): δ=152.1, 151.0, 147.0, 140.3, 130.1, 130.0, 129.4, 127.8, 115.2, 112.6, 77.6, 62.4, 59.5, 49.1, 48.2, 36.9, 33.4, 32.2 and 28.9 ppm. ESI-HRMS for C$_{21}$H$_{28}$N$_5$OS [MH]$^+$ calcd, 398.2015; found, 398.2013.

Example 17: (3R,4S)-4-Butyl-1-[(9-deaza-adenin-9-yl)methyl]-3-hydroxypyrrolidine (20, R=Et)

Example 17.1: tert-Butyl (3R,4S)-4-(but-1-enyl)-3-(tert-butyldimethylsilyloxy)-pyrrolidine-1-carboxylate (17, R=Et)

n-Butyllithium (2.7 mL, 3.8 mmol, 1.4 M solution in hexanes) is added drop-wise to a stirred suspension of n-propyltriphenylphosphonium bromide (1.743 g, 4.52 mmol) in THF (20 mL) at 0° C. After 20 minutes the suspension is cooled to −40° C. and a solution of 6 (for preparation see Example 12.4) (497 mg, 1.5 mmol) in THF (10 mL) is added and the resulting mixture is allowed to warm to −10° C. and kept at that temperature for 30 min. The reaction mixture is then quenched with water (50 mL) and extracted with ethyl acetate (50 mL). The organic layer is separated and washed with water (50 mL) and brine (50 mL) and then dried (MgSO$_4$), filtered and concentrated under reduced pressure. Flash chromatography of the resulting residue (1:19, ETOAc:Petrol) affords 17 (R=Et) as an oil (300 mg, 56%). $^1$H NMR (500 MHz, CDCl$_3$): δ=5.51 (dt, J=10.8, 7.3 Hz, 1H), 5.10 (brt, J=10.1 Hz, 1H), 3.99-3.91 (m, 1H), 3.67-3.58 (m, 1H), 3.56-3.49 (m, 1H), 3.17-2.89 (m, 3H), 2.17-2.00 (m, 2H), 1.45 (s, 9H), 0.97 (t, J=7.6 Hz, 3H), 0.87 (s, 9H) and 0.04 ppm (s, 6H). $^{13}$C NMR (125 MHz, CDCl$_3$): δ=154.6, 135.0, 127.6, 79.3, 76.3, 75.6 (rotamers), 53.0, 52.5 (rotamers), 49.6, 49.2 (rotamers), 45.2, 44.5 (rotamers), 28.6, 25.8, 21.0, 18.1, 14.4 and −4.8 ppm. ESI-HRMS for C$_{19}$H$_{37}$NNaO$_3$Si [MNa]$^+$ calcd, 378.2440; found, 378.2438.

Example 17.3: (3R,4S)-4-Butyl-3-hydroxypyrrolidine (19, R=Et)

A suspension of 17 (R=Et) (260 mg, 0.73 mmol) and Perlman's catalyst (50 mg, cat., 20% b/w) in ethanol (5 mL) is stirred under an atmosphere of hydrogen at room temperature for 18 h. The reaction mixture is then filtered through Celite® and concentrated under reduced pressure to afford, presumably, (3R,4S)-tert-butyl-4-(butyl)-3-(tert-butyldimethylsilyloxy)-pyrrolidine-1-carboxylate (18, R=Et) as a colourless oil. $^1$H NMR confirms the absence of any olefinic protons and compound 18 (R=Et) is committed to the next step without further characterisation or purification. 36% aq. HCl (1 mL, 12 mmol) is added to a solution of 18 (R=Et) (270 mg, 0.76 mmol) in methanol (2 mL) and the resulting solution concentrated under reduced pressure. The resulting residue is dissolved in conc HCl (1 mL, 12 mmol) and concentrated under reduced pressure and the resulting residue partitioned between water (10 mL) and CHCl$_3$ (5 mL). The water layer is washed again with CHCl$_3$ (5 mL) and concentrated under reduced pressure to afford the hydrochloride salt of 19 (R=Et) as a white foam (136 mg, 100%). $^1$H NMR (500 MHz, D$_2$O): δ=4.18-4.14 (m, 1H), 3.47 (dd, J=11.9, 7.4 Hz, 1H), 3.34 (d, J=12.7, 5.3 Hz, 1H), 3.11 (dd, J=12.7, 2.9 Hz, 1H), 2.93 (dd, J=11.9, 6.1 Hz, 1H), 2.16-2.08 (m, 1H), 1.42-1.31 (m, 1H), 1.25-1.14 (m, 5H) and 0.75 ppm (t, J=7.1 Hz, 3H). $^{13}$C NMR (125 MHz, D$_2$O): δ=73.9, 51.1, 48.9, 45.3, 30.1, 29.1, 21.9 and 13.3 ppm. ESI-HRMS for C$_8$H$_{18}$NO [MH]$^+$ calcd, 144.1388; found, 144.1383.

Example 17.4: (3R,4S)-4-Butyl-1-[(9-deaza-adenin-9-yl)methyl]-3-hydroxypyrrolidine (20, R=Et)

Formaldehyde (86 μL, 1.1 mmol, 37 wt % solution in water) followed by 9-deazaadenine (112 mg, 0.84 mmol) are added to a solution of 19 (R=Et) (100 mg, 0.56 mmol) in 1,4-dioxane (1 mL) and water (2 mL). The reaction mixture is warmed to 85° C. and after 1 h the crude reaction mixture absorbed onto silica and eluted down a silica column using a gradient 5-30% (7 N NH$_3$ in MeOH) in CH$_2$Cl$_2$. The crude product is collected, concentrated and subjected to flash chromatography (5:4.5:0.5, CH$_2$Cl$_2$:MeOH:28% aq. NH$_4$OH) to afford 20 (R=Et) as an off-white solid (90 mg, 56%). $^1$H NMR (500 MHz, CD$_3$OD): δ=8.17 (s, 1H), 7.49 (s, 1H), 3.86-3.83 (m, 1H), 3.81 (q, J=13.2 Hz, 2H), 3.05 (dd, J=9.6, 8.0 Hz, 1H), 2.74 (dd, J=10.4, 6.3 Hz, 1H), 2.69 (dd, J=10.4, 4.0 Hz, 1H), 2.17 (dd, J=9.7, 8.0 Hz. 1H), 1.98-1.90 (m, 1H), 1.57-1.47 (m, 1H), 1.34-124 (m, 5H) and 0.89 ppm (t, J=6.9 Hz, 3H). $^{13}$C NMR (125 MHz, CD$_3$OD): δ=152.1, 151.0, 147.0, 130.1, 115.1, 112.6, 77.8, 62.4, 59.7, 49.1, 48.6, 34.0, 31.5, 23.8 and 14.4 ppm. ESI-HRMS for C$_{15}$H$_{24}$N$_5$O [MH]$^+$ calcd, 290.1981; found, 290.1988.

Example 18: (±)-cis-1-[(9-Deaza-adenin-9-yl)methyl]-4-ethyl-3-hydroxypyrrolidine (34)

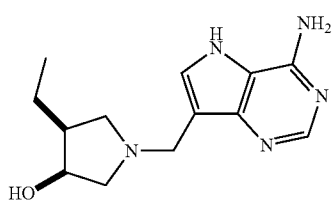

34

Example 18.1: Benzyl (±)-cis-3-(benzoyloxy)-4-ethylpyrrolidine-1-carboxylate (31)

Benzoic acid (430 mg, 3.5 mmol) and triphenylphosphine (909 mg, 3.5 mmol) are added to a stirred solution of 6 (X=ethyl) (719 mg, 2.8 mmol) in THF (24 mL). The reaction mixture is cooled to −10° C. and DIAD (680 μL, 3.5 mmol) is added drop-wise over 10 min. After stirring at −10° C. for 45 min the reaction mixture is warmed to room temperature and stirred for 22 h and then concentrated under reduced pressure. Flash chromatography of the residue (1:9 then 2:8, EtOAc:Petrol) affords 31 as a pale colourless oil (995 mg, 98%). $^1$H NMR (500 MHz, CDCl$_3$): δ=8.12-8.00 (m, 2H), 7.60-7.56 (m, 1H), 7.49-7.28 (m, 7H), 5.57-5.53 (m, 1H), 5.20-5.09 (m, 2H), 3.89-3.67 (m, 3H), 3.29 (dt, J=19.1, 10.7 Hz, 1H), 2.35-2.24 (m, 1H), 1.68-1.46 (m, 2H) and 0.98-0.94 ppm (m, 3H). $^{13}$C NMR (125 MHz, CDCl$_3$): δ=166.0, 165.9, 154.8, 136.9, 136.7, 133.5, 133.3, 133.2, 130.2, 130.0, 129.9, 129.7, 128.5, 128.4, 127.9, 74.7, 73.8 (rotamers), 67.0, 66.9 (rotamers), 53.3, 53.0 (rotamers), 49.8, 49.5 (rotamers), 45.1, 44.3 (rotamers), 20.1 and 12.4 ppm. ESR-HRMS for C$_{21}$H$_{23}$NO$_4$Na [MNa]$^+$ calcd, 376.1525; found, 376.1521.

Example 18.2: Benzyl (±)-cis-4-ethyl-3-hydroxy-pyrrolidine-1-carboxylate (32)

A solution of K$_2$CO$_3$ (583 mg, 4.2 mmol) in water (20 mL) is added to a solution of 31 (995 mg, 2.8 mmol) in ethanol (40 mL). The resulting mixture is heated to reflux for 90 min and then allowed to cool and concentrated under reduced pressure. The residue is partitioned between DCM (50 mL) and water (50 mL) and the layers are separated and the aqueous phase is extracted with EtOAc (3×50 mL). The combined organic phases are washed with brine (2×50 mL), dried (MgSO$_4$), filtered and concentrated under reduced pressure. Flash chromatography of the residue (3:7, EtOAc: Petrol) affords 32 as a yellow oil (476 mg, 68%). $^1$H NMR (500 MHz, CDCl$_3$): δ=7.35-7.29 (m, 5H), 5.15-5.08 (m, 2H), 4.23 (br. s, 1H), 3.67-3.47 (m, 3H), 3.14 (dd, J=10.8, 3.6 Hz, 1H), 2.24 (br. d, J=45 Hz, 1H), 2.01-1.94 (m, 1H), 1.61-1.53 (m, 1H), 1.51-1.43 (m, 1H) and 0.98-0.94 ppm (m, 3H). $^{13}$C NMR (125 MHz, CDCl$_3$): δ=155.2, 155.0, 136.9, 128.4, 127.9, 127.8, 71.7, 70.7 (rotamers), 66.8, 66.7 (rotamers), 55.5, 55.0 (rotamers), 49.0, 48.8 (rotamers), 46.0, 45.3 (rotamers), 19.6 and 12.4 ppm. ESI-HRMS for C$_{14}$H$_{19}$NO$_3$Na [MNa]$^+$ calcd, 272.1263; found, 272.1268.

Example 18.3: (±)-cis-4-Ethyl-3-hydroxypyrrolidine (33)

Palladium (10 mg, 0.01 mmol, 10 wt % on carbon) is added to a solution of 32 (146 mg, 0.5 mmol) in MeOH (10 mL) under argon. The reaction mixture is placed under a hydrogen atmosphere and stirred for 1 h and then filtered through Celite® and concentrated under reduced pressure. Flash chromatography of the residue (gradient 10 to 40% (7N NH$_3$ in MeOH) in DCM) affords 33 as a yellow oil (42 mg, 62%). $^1$H NMR (500 MHz, CD$_3$OD): δ=4.17 (td, J=4.5, 1.4 Hz, 1H), 3.04 (dd, J=12.2, 4.4 Hz, 1H), 2.99 (dd, J=10.5, 7.9 Hz, 1H), 2.84 (dd, J=12.2, 1.3 Hz, 1H), 2.61 (t, J=10.6 Hz, 1H), 1.86-1.79 (m, 1H), 1.65-1.56 (m, 1H), 1.46-1.37 (m, 1H) and 0.98 ppm (t, J=7.4 Hz, 3H). $^{13}$C NMR (125 MHz, CD$_3$OD): δ=73.2, 56.0, 50.6, 48.6, 21.0 and 13.3 ppm. ESI-HRMS for C$_6$H$_{14}$NO [MH]$^+$ calcd, 116.1075; found, 116.1077.

Example 18.4: (±)-cis-1-[(9-Deaza-adenin-9-yl)methyl]-4-ethyl-3-hydroxypyrrolidine (34)

Formaldehyde (35 μL, 0.4 mmol, 37 wt % solution in water) followed by 9-deazaadenine (52 mg, 0.4 mmol) are added to a solution of 33 (32 mg, 0.3 mmol) in 1,4-dioxane (1 mL) and water (1 mL). The reaction mixture is stirred at room temperature for 68 h, absorbed onto silica and eluted down a silica column using a gradient 10-50% (7 N NH$_3$ in MeOH) in CH$_2$Cl$_2$. The crude product is collected, concentrated and subjected to flash chromatography (5:4.9:0.1 then 5:4.8:0.2, CH$_2$Cl$_2$:MeOH: 28% aq. NH$_4$OH) to afford 34 as an off-white solid (45 mg, 62%). $^1$H NMR (500 MHz, CD$_3$OD): δ=8.16 (s, 1H), 7.49 (s, 1H), 4.20 (td, J=5.8, 3.3 Hz, 1H), 3.89 (s, 2H), 3.17 (dd, J=10.9, 5.5 Hz, 1H), 2.95 (dd, J=9.4, 7.5 Hz, 1H), 2.57 (dd, J=10.9, 3.3 Hz, 1H), 2.41 (t, J=9.9 Hz, 1H), 2.00-1.92 (m, 1H), 1.61-1.53 (m, 1H), 1.38-1.28 (m, 1H) and 0.92 ppm (t, J=7.5 Hz, 3H). $^{13}$C NMR (125 MHz, CD$_3$OD): δ=152.1, 151.0, 147.0, 130.1, 115.1, 112.7, 72.5, 63.0, 58.3, 49.4, 46.6, 21.4 and 13.2 ppm. ESI-HRMS for C$_{13}$H$_{20}$N$_5$O [MH]$^+$ calcd, 262.1668; found, 262.1663.

Example 19: Inhibition Studies

*E. coli* MTAN and human MTAP are obtained according to reported methods (Singh, et al, *Biochemistry* 44, 11647-

11659 (2005); Singh and Schramm *J. Am. Chem. Soc.* 128, 14691-14696 (2006). The MTAN gene sequences from *N. meningitides* MC58 and *H. pylori* J99 are amplified from genomic DNA (ATCC) and cloned into a modified pET-32 vector to direct high-level expression of MTAN with a non-cleavable N-terminal 6 His tag. 1.5 L cultures of BL21 (DE3) harbouring MTAN constructs are induced with 0.5 mM IPTG for 20 hours at 25° C. with vigorous shaking. Cell pellets are washed and lysed in 40 mL lysis buffer (25 mM HEPES, 0.5M NaCl, 10 mM imidazole pH 7.6, protease inhibitors and 0.25 mM TCEP) with the use of a cell disrupter at 15K psi. After removal of cell debris by centrifugation, the soluble cell lysates are loaded onto nickel-charged chelating Sepharose (GE Healthcare) and washed with lysis buffer containing 20-150 mM imidazole. The 6His-MTANs are eluted in 250 mM imidazole, desalted using a Sephadex G-15 (GE Healthcare) gel filtration column, equilibrated with low salt buffer (100 mM HEPES, 30 mM KCL, pH 7.6) and concentrated to 40 mg/mL.

Inhibitor concentrations are obtained from the absorbance at 274 nm with extinction coefficient of 8.5 mM$^{-1}$ cm$^{-1}$ for the 9-deazaadenine moiety.

Continuous spectrophotometric assays are used to characterize the compounds of the invention and in vivo inhibition of MTAP. The conversion of MTA into adenine is measured as a decrease in absorbance at 274 nm. At 274 nm, the difference in spectral properties is maximum and the millimolar extinction coefficient (cm$^{-1}$) is 1.6 for the conversion of MTA to adenine.

MTAN activities are assayed as reported (Singh et al (2006) *Biochemistry* 45, 12929-12941; Singh, et al (2005) *J. Biol. Chem.* 280, 18265-18273). Briefly, all experiments are carried out at 25° C., in 1 mL total reaction volume containing 100 mM HEPES buffer, pH 7.5 and 50 mM KCl with 5'-deoxymethylthioadenosine (MTA) as substrate. Kinetic constants ($k_{cat}$ and $K_m$) are determined by monitoring MTA hydrolysis at 274 nm where $\Delta\varepsilon_{MTA}$=1.6 mM$^{-1}$ cm$^{-1}$. For measuring dissociation constant ($K_d$) of inhibitors, a xanthine oxidase-coupled assay is carried out. In this assay, saturating levels (1-2 mM) of MTA and various concentrations of inhibitor are mixed with xanthine oxidase (0.5 unit/mL), which is used to convert the MTAN product adenine to 2,8-dihydroxyadenine ($\varepsilon2$, 8-dihydroxadenine=15.2 mM$^{-1}$ cm$^{-1}$ at 293 nm). Reactions are initiated by the addition of 8-10 nM MTAN, and the absorbance at 293 is monitored. Control experiments are carried out in the absence of either inhibitor or MTAN. Slow onset dissociation constants $K_d$ in the presence of more than 10-fold excessive inhibitor are obtained using the following equation:

$$v'_s/v_s = \frac{K_m + [S]}{K_m + [S] + K_m[I]/K_d}$$

where $v_s^t$ and $v_s$ are steady state rates in the presence, and absence of inhibitor, respectively; $K_m$ is substrate Michaelis constant which is obtained as described above; [S] and [I] are the concentrations of the substrate MTA and inhibitor, respectively. If the concentration of inhibitor is smaller than 10-fold concentration of enzymes, the following correction is then applied:

$$I=I'-(1-v_0'/v_0)E_t$$

where I' is the effective inhibitor concentration; I is the concentration of inhibitor used in the assay; $v_0'$ and $v_0$ are initial rates in the presence, and absence of inhibitor, respectively; and $E_t$ is total MTAN concentration used in the assay. All data fitting is carried out with KaleidaGraph™ ver. 3.5 (Synergy Software).

TABLE 1

Inhibition Constants with MTAP, *E. coli* MTAN, and *N. meningitidis* MTAN

| | | Enzyme and Inhibition ($K_i$, nanomolar) | | |
|---|---|---|---|---|
| Example No | Compound | *E. coli* MTAN | *N. meningitides* MTAN | Human MTAP |
| Compounds of Formula I Where A = CH, B = NH$_2$, D = H and X is: | | | | |
| 1 | Phenyl | *0.030 ± 0.002 | *0.24 ± 0.02 | 4.3 ± 0.6 |
| 2 | Cyclohexylmethyl | 0.059 ± 0.008 | *0.31 ± 0.05 | >5 μM |
| 4 | Cyclopropyl | 0.063 ± 0.005 | 0.5 ± 0.1 | 5.8 ± 0.7 |
| 5 | Vinyl | 0.65 ± 0.03 | 0.7 ± 0.1 | 8.7 ± 1.0 |
| 6 | Allyl | 0.35 ± 0.03 | 3.0 ± 0.2 | 14.3 ± 1.7 |
| 7 | Ethynyl | 0.39 ± 0.02 | — | 31 ± 3 |
| 8 | Butyl | 0.051 ± 0.003 | 0.47 ± 0.06 | >5 μM |
| 9 | Isobutyl | *0.047 ± 0.009 | *0.28 ± 0.06 | 6.0 ± 0.4 |
| 10 | Pent-3-yl | 0.7 ± 0.1 | *0.44 ± 0.08 | >5 μM |
| 11 | Ethyl | 0.31 ± 0.02 | 2.2 ± 0.3 | 8.6 ± 1.0 |
| 13 | Cyclopentyl | *0.013 ± 0.001 | — | 2.4 ± 0.4 |
| 14 | 1-Benzy-1,2,3-triazol-4yl | *0.064 ± 0.005 | | a |
| 15 | 1,2,3-Triazol-1-yl | 2.0 ± 0.2 | — | 59 ± 8 |
| 16 | 3-(Benzylthio)-propyl | *0.054 ± 0.005 | — | 71 ± 5 |
| Other compounds | | | | |
| 12 | Compound 20, R = H), the (3R,4S)-4-Ethyl analogue | 0.84 ± 0.06 | 1.4 ± 0.2 | >5 μM |

TABLE 1-continued

Inhibition Constants with MTAP, *E. coli* MTAN, and *N. meningitidis* MTAN

| | | Enzyme and Inhibition ($K_i$, nanomolar) | | |
|---|---|---|---|---|
| Example No | Compound | *E. coli* MTAN | *N. meningitides* MTAN | Human MTAP |
| 17 | Compound 20, R = Et), the (3R,4S)-4-Butyl analogue | *0.0034 ± 0.0009 | — | 0.55 ± 0.07 |
| 18 | Compound 34, the (±)-cis-4-Ethyl analogue | 1.8 ± 0.3 | — | 34 ± 3 |

*indicates slow onset binding.
$^a$ indicates no inhibition observed at 2.5 μM.

Although the invention has been described by way of example, it should be appreciated the variations or modifications may be made without departing from the scope of the invention. Furthermore, when known equivalents exist to specific features, such equivalents are incorporated as if specifically referred to in the specification.

INDUSTRIAL APPLICABILITY

The invention relates to compounds that are inhibitors of MTAP and/or MTAN. The compounds are therefore indicated for the treatment or prevention of diseases in which the inhibition of MTAP or MTAN is desirable, e.g. cancer and bacterial infections.

The invention claimed is:
1. A compound of the formula (Ia):

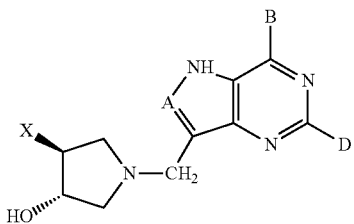

where:
X is ethyl;
A is CH;
B is $NH_2$ or $NHR^5$;
$R^5$ is an alkyl, alkenyl, alkynyl, aralkyl, aralkenyl, aralkynyl, or aryl group, each of which is optionally substituted with one or more halogen or hydroxy groups; and
D is H, OH, $NH_2$, or $SCH_3$;
or a tautomer thereof, or a pharmaceutically acceptable salt thereof, or an ester prodrug form thereof.

2. A compound as claimed in claim 1 which is a compound of the formula (Ib):

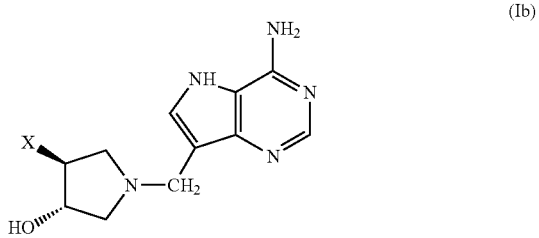

or a tautomer thereof, or a pharmaceutically acceptable salt thereof, or an ester prodrug form thereof.

3. A compound as claimed in claim 1 where B is $NH_2$.
4. A pharmaceutical composition comprising a pharmaceutically effective amount of a compound as claimed in claim 1.
5. A method of inhibiting 5'-methylthioadenosine phosphorylase (MTAP) or 5'-methylthioadenosine nucleosidase (MTAN) in a subject comprising contacting the MTAP or MTAN with a compound as claimed in claim 1 in an amount effective to inhibit MTAP or MTAN.
6. The method of claim 5, wherein the MTAP or MTAN is in a human subject.
7. The method of claim 6, wherein the subject has cancer or a bacterial or protozoal infection.
8. A method of inhibiting 5'-methylthioadenosine phosphorylase (MTAP) or 5'-methylthioadenosine nucleosidase (MTAN) comprising contacting the MTAP or MTAN with a compound as claimed in claim 1 in an amount effective to inhibit MTAP or MTAN.

* * * * *